United States Patent [19]

Shirota et al.

[11] Patent Number: 5,738,783
[45] Date of Patent: Apr. 14, 1998

[54] LIQUID CHROMATOGRAPH HAVING A MICRO- AND SEMI-MICRO COLUMN

[75] Inventors: Osamu Shirota; Taketoshi Kanda; Ayako Suzuki; Yutaka Ohtsu; Michihiro Yamaguchi, all of Yokohama; Hisao Tsuruta, Kyoto; Ryujiro Namba, Yokohama, all of Japan

[73] Assignee: Shiseido Company, Ltd., Tokyo, Japan

[21] Appl. No.: 766,602

[22] Filed: Dec. 12, 1996

Related U.S. Application Data

[63] Continuation of Ser. No. 337,659, Nov. 10, 1994, abandoned.

[30] Foreign Application Priority Data

| May 9, 1994 | [JP] | Japan | 6-095270 |
| May 13, 1994 | [JP] | Japan | 6-099515 |
| Jun. 3, 1994 | [JP] | Japan | 6-122702 |
| Sep. 30, 1994 | [JP] | Japan | 6-236576 |

[51] Int. Cl.$^6$ .................................................. B01D 15/08
[52] U.S. Cl. ........................ 210/198.2; 210/502.1; 210/635; 210/656
[58] Field of Search .......................... 210/635, 656, 210/198.2, 502.1; 502/401, 402; 422/70

[56] References Cited

U.S. PATENT DOCUMENTS

| 4,577,492 | 3/1986 | Holba et al. | 210/198.2 |
| 4,743,377 | 5/1988 | Ohtsu | 210/198.2 |
| 5,135,649 | 8/1992 | Kanda | 210/198.2 |
| 5,203,991 | 4/1993 | Kutsuna | 210/198.2 |
| 5,277,813 | 1/1994 | Feibush et al. | 210/502.1 |

FOREIGN PATENT DOCUMENTS

| A-0092860 | 11/1983 | European Pat. Off. | 210/198.2 |
| A-0495255 | 7/1992 | European Pat. Off. | 210/198.2 |
| 60-56256 | 4/1985 | Japan | 210/198.2 |
| 61-65159 | 4/1986 | Japan | 210/198.2 |
| 1-123145 | 5/1989 | Japan | 210/198.2 |
| A-2084887 | 4/1982 | United Kingdom | 210/198.2 |

OTHER PUBLICATIONS

Patent Abstracts of Japan, vo. 10, No. 38 (P–428) (2095), Feb. 14, 1986 an abstract of JP–A–60 183 554 (Hitachi Seisakusho K.K.) filed Mar. 1, 1984.

Haginaka, J., et al. J. Chromatogr. 529 (1990) 455–461, Elsevier Science Publishers B.V.

Patent Abstracts of Japan, vol. 17, No. 399 (P01579) Jul. 26, 1993 & JP–A–05 072 190 (Shiseido).

Chemometrics and Intelligent Laboratory Systems, vol. 17, No. 2, Nov. 1992, Amsterdam, NL pp. 233–242, XP3225665, L.–E. Edholm, et al., 'automated bioanalysis of drugs using coupled column liquid chromatography for sample pretreatment—aspects of quality assurance and collaborative automated handling of data'.

Trac, Trends In Analytical Chemistry., vol. 6, No. 5, Jun. 1987, Cambridge GB pp. 134–138 H.M. Ruijten, et al.

(List continued on next page.)

*Primary Examiner*—Ernest G. Therkorn
*Attorney, Agent, or Firm*—Kenyon & Kenyon

[57] ABSTRACT

A liquid chromatograph includes pumps for supplying solvents, a mixer for mixing the solvents, a controller for controlling a mixing ratio of the solvents in the mixer, a chromatograph column for separating a sample carried with the solvents, a flow path control valve for supplying the sample together with the solvents to the chromatograph column, and a detector for detecting the sample supplied thereto, wherein the mixer includes a mixing chamber and a porous medium accommodated in the mixing chamber, the porous medium having a size and shape in conformity with a size and shape of said mixing chamber such that no substantial gap is formed between an outer surface of the porous medium and an inner surface of the mixing chamber.

3 Claims, 31 Drawing Sheets

OTHER PUBLICATIONS

Scott, R.P.W., et al., "The Exclusion Properties of Some Commerically Available Silica Gels," *Journal of Chromatography*, vol. 125, pp. 251–263, 1976.

Ishii, D., et al., "A Study of Micro–High–Performance Liquid Chromatography," *Journal of Chromatography*, vol. 144, pp. 157–168, 1977.

Novotny, Milos, "Recent Advances in Microcolumn Liquid Chromatography," *Analytical Chemistry*, vol. 60, Apr. 15, 1988, pp. 500–510.

Tsuda, Takao, et al., "Band–Broadening Phenomena in Microcapillary Tubes Under the Conditions of liquid Chromatography," *Analytical Chemistry*, vol. 50, Apr. 1978, pp. 632–634.

Snyder, Introduction to Modern Liquid Chromatography, John Wiley & Sons, Inc, 1979, New York, pp. 228–230.

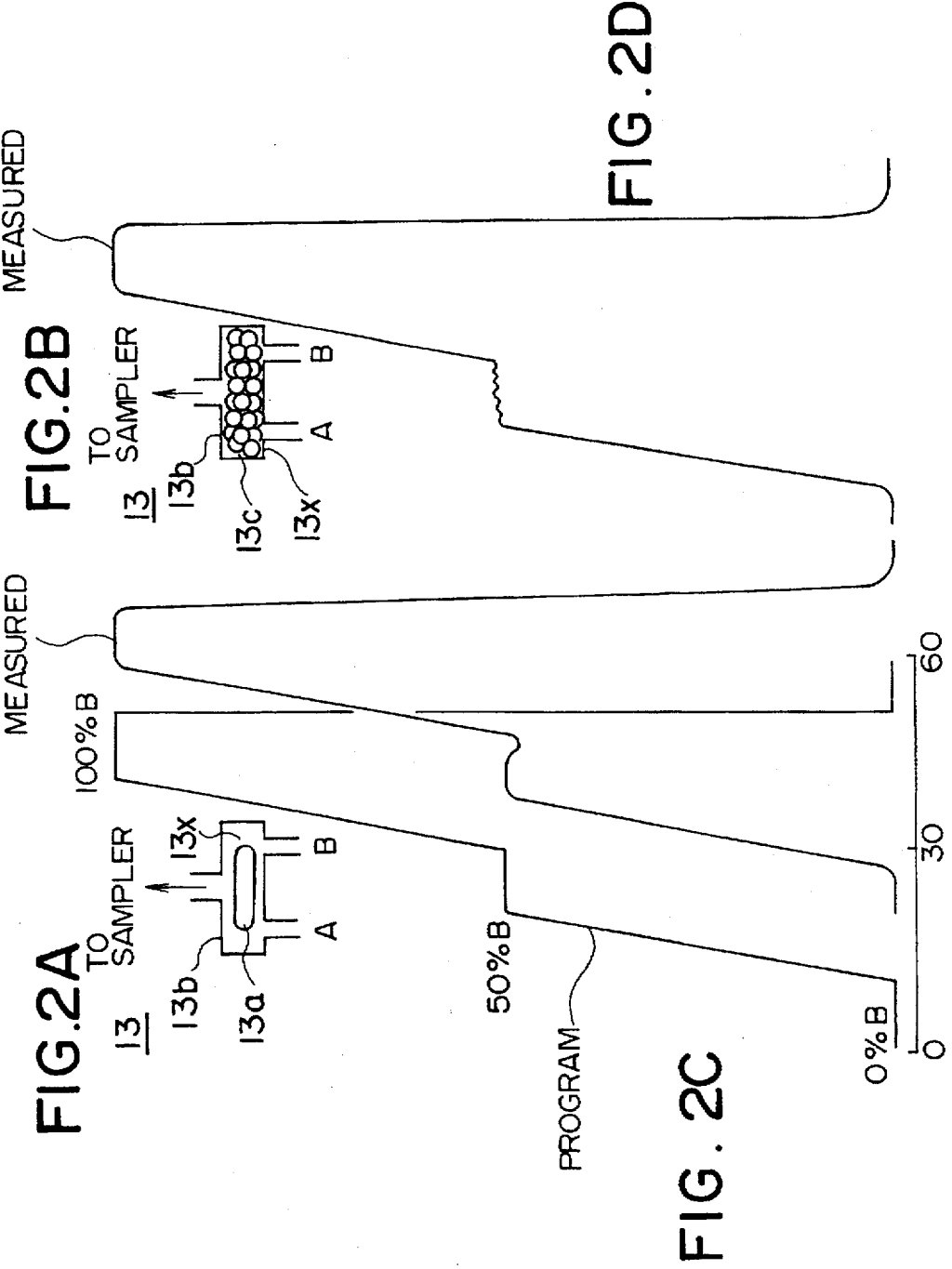

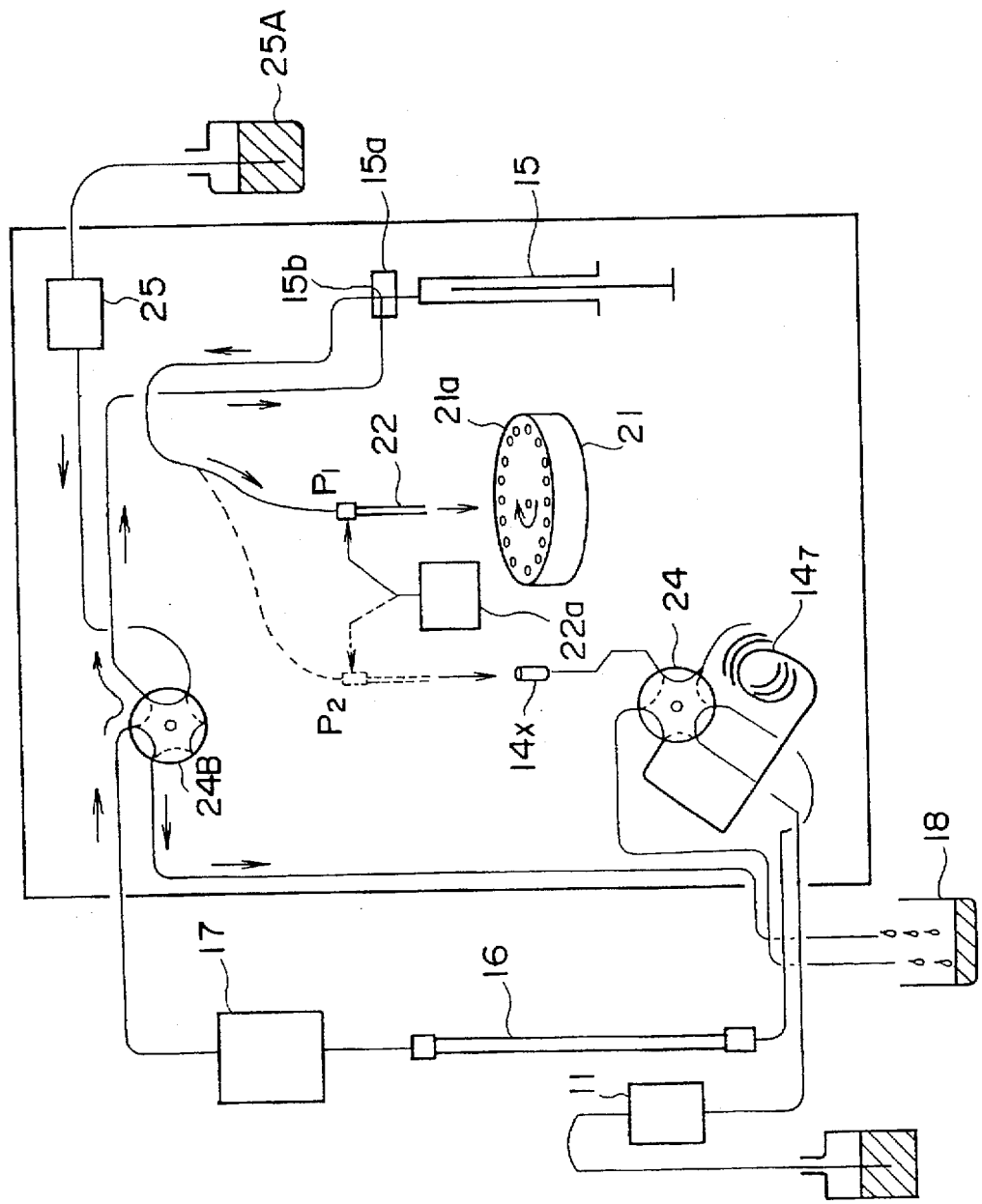

FIG. 29A
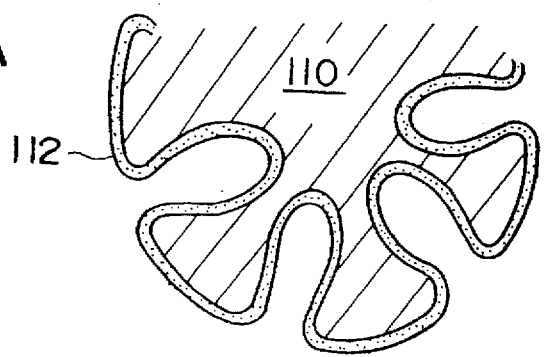
FIG. 29B
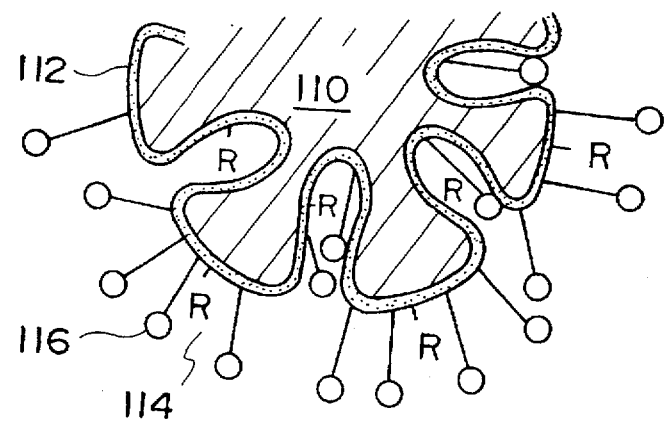

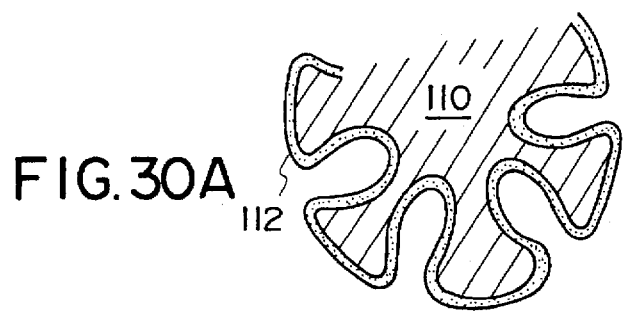
FIG. 30A
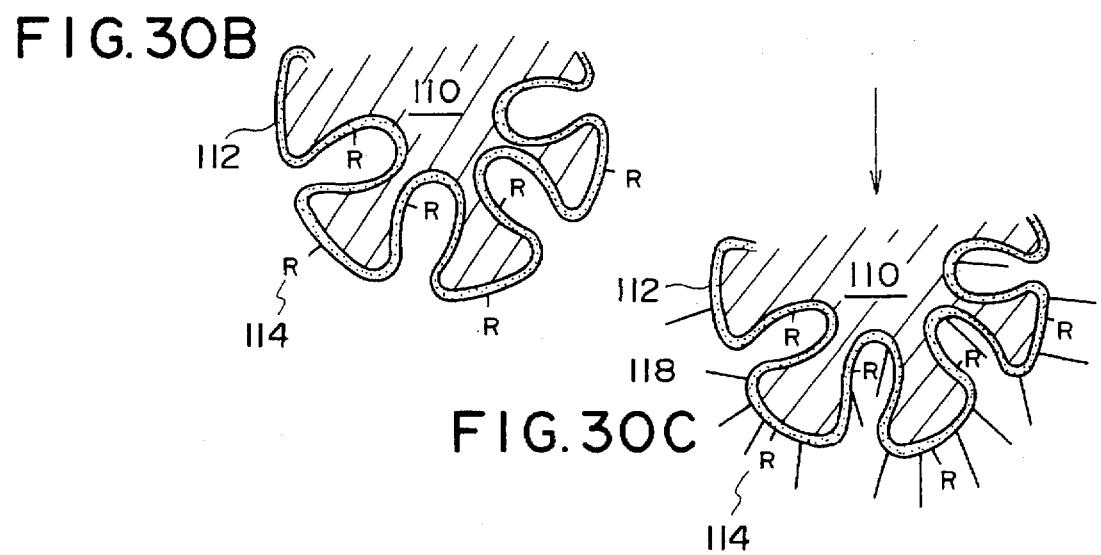
FIG. 30B
FIG. 30C
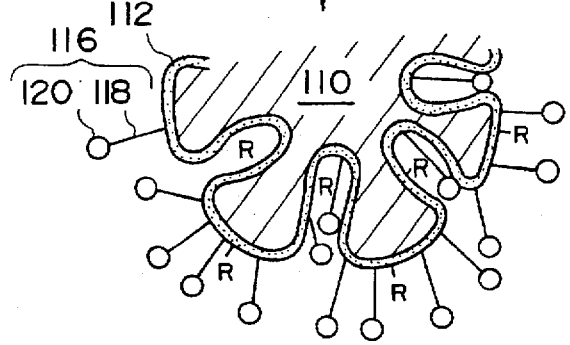
FIG. 30D

LIQUID CHROMATOGRAPH HAVING A MICRO- AND SEMI-MICRO COLUMN

This application is a filewrapper continuation of application Ser. No. 08/337,659 filed on Nov. 10, 1994, now abandoned.

BACKGROUND OF THE INVENTION

The present invention generally relates to liquid chromatographs and more particularly to a liquid chromatograph that uses a semi-micro column or micro column.

Liquid chromatographs are used extensively as a means for separating and analyzing chemical substances. Particularly, a liquid chromatograph that uses semi-micro column or micro column having an inner diameter of 1–2 mm or less is studied intensively in view of advantageous feature of high sensitivity, high resolution and high precision analysis.

In the art of liquid chromatography, the so-called gradient elution is employed commonly, wherein the composition of the solvent flowing through the column is changed with time. In the gradient elution, it is particularly necessary to control the composition of the solvent exactly, and because of this, a mixer is used for mixing a plurality of solvents.

When using semi-micro-columns having a small diameter for the gradient elution, it is necessary to set the flow rate of the fluid acting as the mobile phase in the column to be small, in the order of one-fifth to one-tenth or less, as compared with the flow rate employed in the conventional liquid chromatographs. Associated with this, there occur various problems to be solved.

FIG. 1 is a block diagram showing the schematic construction of a conventional liquid chromatograph designed for the gradient elution.

Referring to FIG. 1, the liquid chromatograph includes a first pump 11A for pumping a first solvent A and a second pump 11B for pumping a second solvent B, wherein the pumps 11A and 11B, respectively, supply the solvents A and B to a mixer 13 under control of a system controller 12. After mixing in the mixer 13 to a desired mixing ratio, the mixture of the solvents A and B are supplied to a sampler 14 wherein a sample solution held in a syringe 15 is injected to the mixture thus formed. The sample solution contains various chemical substances to be analyzed. Thereafter, the sample solution is supplied, together with the solvent A and/or B, to a column 16. Upon passage through the column 16, chemical substances in the sample solution are separated and supplied to a detector 17 together with the solvent. The detector 17, in turn, carries out a qualitative and/or quantitative analysis of the chemical species contained in the solvents A and/or B. After analysis in the analyzer 17, the solvents and the chemical substances are ejected to a waste reservoir 18.

FIGS. 2A and 2B show various constructions of the mixer 13 used in the liquid chromatograph of FIG. 1.

Referring to FIG. 2A, the mixer 13 mixes the solvents A and B in a chamber 13b by means of a rotating stirrer 13a. However, the mixer 13 of FIG. 2A tends to create a dead space 13x along the vessel wall of the chamber 13b wherein no substantial mixing occurs. In the low flow rate system such as the semi-micro-column liquid chromatograph, the effect of the dead space 13x appears particularly conspicuous.

FIG. 2C shows the mixing characteristic of the mixer 13 of FIG. 2A for a case in which methanol is used for the solvent A and a mixture of methanol and a small amount of acetone (0.05 volumetric percent) is used for the solvent B. In the measurement of the mixing characteristic, the mixing ratio is controlled stepwise according to a program curve shown at the left of FIG. 2C while simultaneously detecting the acetone content in the solvents thus mixed. The curve at the right of the program curve represents the actual or measured mixing ratio.

In the experiment, only the solvents A and B are caused to flow through the column 16 under the total flow rate set to 200 μm/min. Further, the detection of acetone is made by measuring the ultraviolet absorption at the wavelength of 245 nm. In the example of FIGS. 2A and 2C, it will be noted that there occurs a momentary drop in the measured mixing ratio when the programmed mixing ratio is increased linearly and subsequently held at a level of 50%. Further, it should be noted that the actual characteristic curve at the left of the program curve generally has a rounded shoulder, indicating that the mixing cannot follow the program control.

The mixer 13 of FIG. 2B is proposed for eliminating the foregoing problem of the mixer of FIG. 2A.

Referring to FIG. 2B, the chamber 13b of the mixer is filled with small beads 13c, and the solvents A and B are caused to flow through irregular paths of fluid formed between the beads. By employing the construction as such, the problem of irregular mixing ratio associated with the stepwise change of the program mixing ratio is successfully eliminated as indicated in FIG. 2D, wherein FIG. 2D shows the result of measurement of the acetone content in the mixture of the solvents. In FIG. 2D, it should be noted that the mixing of the solvents A and B is carried out according to the same program curve shown in FIG. 2C. On the other hand, the problem of rounded shape of the actual mixing characteristic curve is not eliminated completely even in the case of FIG. 2D corresponding to the construction of the mixer 13 of FIG. 2B, indicating that there still exists a dead space 13x in the chamber 13b in which no substantial mixing of the solvents occurs.

FIGS. 3A and 3B show the construction of the sampler 14 used in the liquid chromatograph of FIG. 1.

Referring to FIG. 3A, the sampler 14 is essentially formed of a six-port valve including a rotary valve body 14R, wherein the rotary valve body 14R is formed with six passages $14_1$–$14_6$, and there are formed three interconnecting passages 14a–14c each connecting two of the foregoing six passages $14_1$–$14_6$. In the illustrated state of FIG. 3A, the passage 14a connects the passages $14_1$ and $14_6$ with each other, the passage 14b connects the passages $14_2$ and $14_3$ with each other, and the passage 14c connects the passages $14_5$ and $14_6$ with each other. In the state of FIG. 3A, it should be noted that the passage $14_1$ is aligned to a port P that in turn is connected to the mixer 13, the passage $14_2$ is aligned to a part $A_1$ connected to an end of a sample accumulation loop $14_7$ to be described later, the passage $14_3$ is aligned to a port S connected to the syringe 15, the passage $14_4$ is aligned to a port D connected to the waste reservoir 18, the passage $14_5$ is aligned to a port $A_2$ connected to the other end of the loop $14_7$, and the passage $14_6$ is aligned to a port C connected to the column 16. As a result, the solvents A and B from the mixer 13 are supplied to the column 16 via the foregoing passages $14_1$, 14a and $14_6$, consecutively. In other words, only the solvents are supplied to the column in the state of FIG. 3A. No sample solution is supplied. Further, in the state of FIG. 3A, it should be noted that the syringe 15 communicates with the loop $14_7$ via the passages $14_3$, 14b and $14_2$, while the loop $14_7$ communicates with the waste reservoir 18 via the passages $14_5$, 14c and $14_4$. Thus, the sample solution is injected from the syringe 15 to the loop $14_7$ in the state of FIG. 3A and held therein.

In the state of FIG. 3B, on the other hand, the rotary valve body 14R is rotated in the direction of arrow, and as a result, the port P now aligns to the loop $14_7$ via the passages $14_2$, 14b and $14_3$. Further, the port C aligns to the passages $14_1$, 14a and $14_6$. As a result, the solvent supplied from the mixer 13 carries the sample solution, held in the loop $14_7$, to the column 16 via the port C. In other words, injection of the sample solution to the column 16 is carried out. Further, the syringe 15 is connected to the waste reservoir 18 via the passages $14_4$, 14c and $14_5$.

FIG. 4 shows the construction of the six-port valve 14 in an exploded view.

Referring to FIG. 4, the six-port valve 14 includes a stationary cap 14S acting as a stationary member on which the rotary valve body 14R is mounted rotatably. Further, the six-port valve 14 includes another valve body $14R_2$ that carries the foregoing passages 14a–14c. The rotary valve 14R carries thereon the passages $14_1$–$14_6$ in the form of straight, tubular passages, while the cap 14C carries the foregoing ports P, $A_1$, S, D, $A_2$ and C in alignment with the passages in the rotary valve body 14R. By rotating the rotary valve 14R with respect to the stationary cap 14S, the switching of the passage of fluid described with reference to FIGS. 2A and 2B is achieved.

In the six-port valve 14 of FIG. 4, it should be noted that the passages 14a–14c on the valve body $14R_2$ are generally formed with a tolerance such that passages $14_1$–$14_6$ align positively with the corresponding passages 14a–14c, even in the case where there exists an error in the precision of machining the passages. On the other hand, such a tolerance invites an increase in the size of the passages 14a–14c as indicated in FIG. 5, wherein it will be noted that a dead space 14ax is formed such that a part of the sample solution supplied to the loop $14_7$ from the mixer 13 dwells in such a dead space. Such a dead space 14ax inevitably invites incomplete supply of the sample solution to the column 16, and there occurs an error in the detection carried out by the detector 17.

In the liquid chromatograph of FIG. 1, it should further be noted that there exist a case in which collection of the sample solution separated by the column 16 is wished for various purposes. In order to meet such a demand, there is a construction of liquid chromatograph in which the sample solution is collected in a sample vessel after the analysis by the detector 17, rather than wasting the same to the waste reservoir 18. On the other hand, the sample solution obtained from the detector 17 is diluted by the solvents, and such a construction to recover the diluted waste solution generally requires an extensive facility. Thereby, the construction of the liquid chromatograph becomes inevitably large.

In the liquid chromatograph of FIG. 1, it should be noted that the rotary valve body 14R of FIG. 4 has been generally actuated by a stepping motor. Thus, the stepping motor rotates, in response to an external drive control signal, with a predetermined angle, and the switching of the fluid passage is achieved as a result. In the conventional six-port valve of FIG. 4, the cap 14S, the valve body 14R and the valve body $14R_2$ are all formed of metal in view of mechanical durability and durability against abrasion. Thus, the conventional liquid chromatograph requires an external controller such as a microcomputer for driving the stepping motor, and the construction for recovering the sample solution after the analysis can be realized only in those apparatuses having such a microcomputer as a controller. Further, because of the fact that the valve 14 is formed of metals, the conventional valve 14 is vulnerable to corrosion caused by the sample solution or solvents, and there has been a substantial risk that the result of analysis is unreliable due to the contamination caused by the corrosion of the valve 14. Further, the operation of the valve 14 may become unreliable due to the corrosion or wear.

FIG. 6 shows a sample injection needle 22 provided in the sampler 14 for injecting the sample solution to the column 16. In FIG. 6, the sample solution is indicated by a matting 30. Further, the injection needle 22 is used for injecting a cleaning solution 31 when the liquid chromatograph is in the cleaning mode. The needle 22 is provided at an end of a tube 32 extending to the syringe 15, wherein it will be noted that the connection between the needle 22 and the tube 32 is achieved by an intervening member 37. Conventionally, the cleaning solution is filled in the injection needle 22 as well as in the tube 32 prior to the injection of the sample solution 23, and a suction of the air is made to form an air gap 33 in the needle 22. Next, the suction of the sample solution 30 is made, and a suction of the air is made again to form a second air gap 34 in the needle 22. Thereby, it will be noted that the sample solution 30 is sandwiched by the air gaps 33 and 34 in the injection needle 22, and the injection of the sample solution 30 is made into the column 16 together with the gaps 33 and 34.

In the conventional process of sample injection shown in FIG. 6, it will be noted that the sample solution 30 may be adsorbed on the inner wall of the piping extending to the column 16, when an injection of the sample solution 30 is made. Thereby, there is a possibility that the sample solution 30 that reaches the column 16 and further to the detector 17 is lost by an amount corresponding to those adsorbed on the inner wall of the piping, and there is a problem that such a decrease of the sample causes an error in the result of the measurement. This problem of error becomes particularly pronounced in the chromatographs in which the amount of injected sample solution is small, in the order of 2 μl or less.

FIG. 7 shows a conventional dual-column liquid chromatographic separation system, wherein there is provided a prefocusing column (precolumn) 40 between an automatic sampler 14 and a six-port switching valve 10, wherein the syringe 15 described before and a cooperating mechanism are collectively designated by the reference numeral 14. Further, a solvent-pumping system including the pumps 11A and 11B cooperates with the six-port valve 10. In the construction of FIG. 7, the precolumn 40 concentrates a sample or target substance that has been injected by the sample injector into a solvent A supplied by the pump 11A, and the substance thus concentrated is transferred further to the secondary column (separation column) 16 for separation together with a solvent B supplied by the pump 12. Thereby, the switching of the solvents A and B is achieved by the foregoing six-port valve 10. The transferred substances are separated and detected by the detector 17 cooperating with the separation column 16. Such a dual-column system is advantageous in view of elimination of sample treatment prior to the analysis and is commonly used as a "sample-treatment-free" system.

More specifically, the six-port valve 10 is switched between a first state and a second state, wherein, in the first state, the sample injected to the solvent A by the autosampler 14 is fed to the valve 10 after passing through the precolumn 40 and forwarded further to a waste reservoir along a path indicated by a continuous line, wherein the sample alone is captured by the precolumn 40. Simultaneously, the solvent B is supplied to the valve 10 and forwarded to the separation column 16 along another continuous line shown in FIG. 7.

In the second state, on the other hand, the concentrated sample from the precolumn 40 is now caused to flow to the separation column 16 along a path shown by a broken line in FIG. 7 for analysis, while the solvent B from the pump 2 is caused to flow to the waste reservoir along a path shown by another broken line. In such a conventional system, there has been a problem of dead volume in the valve 10. Because of the existence of such a dead volume, the switching of the fluid in the six-port valve 10 has not been complete.

It should be noted that the condensation column 40 is filled with a packing material that carries out the desired condensation of the sample solution. On the other hand, there is a tendency that such a packing material used in the condensation column 40 causes an adsorption of proteins, particularly when the liquid chromatograph is used for separation and analysis of mixtures that contain a large amount of proteins such as a serum. The adsorption of the proteins on the filler causes a substantial decrease in the effectiveness of the column filler for concentrating the sample solution. Conventionally, therefore, a process has been necessary for removing the proteins from the sample solution before it is supplied to the condensation column 40. Such a preparation of the sample solution, of course, is undesirable in view of extraneous time needed and possible degradation in the precision or reliability of the analysis.

Thus, there are proposals for the column filler for use in the condensation column 40 in which the necessity for removing proteins from the sample solution is eliminated. Generally, such improved column fillers are based upon porous glass or silica gel, and a material having a property different from that of the column filler is provided inside the minute pores of the filler. As a result, macro-molecules such as proteins in the serum cannot invade into the pores of the filler but simply pass through the condensation column 40 without being adsorbed upon the hydrophilic outer surface of the filler. Only small molecules such as the molecules of drugs are adsorbed on the hydrophobic inner surface of the pores.

The Japanese Laid-open Patent Publication 60-56256 describes an example of such an improved filler. In the filler disclosed in the foregoing prior art reference, a protein covers the outer surface of a silica body on which octadecylsilil (ODS) is bonded. The protein used herein may be bovine serum albumin and modifies the silica surface thus treated with ODS. In the conventional filler described above, however, there occurs a problem in that the adsorbed protein is generally released from the surface after prolonged use. Further, such a conventional filler cannot provide a column having high efficiency of separation.

In order to improve deficiency of such conventional column fillers, there are various proposals, as in the Japanese Laid-open Patent Publications 61-65159 and 1-123145, to treat the porous medium forming the filler by introducing hydrophobic groups upon the inner as well as outer surfaces of porous medium, and selectively disconnecting and removing the hydrophobic groups from the outer surface of the porous medium by means of enzyme. It should be noted that enzyme is a macro-molecule and cannot invade the interior of the minute pores of the medium forming the filler. Further, a hydrophilic group is introduced to the outer surface of the porous medium.

In the process of the foregoing '159 publication, in particular, a porous silica medium infiltrated with glyceryl propyl group is used as a starting material, and oligopeptide is bonded thereto via carbonyl diimidazole. Further, the phenylalanine side chains on the outer surface of the silica medium are disconnected by means of carboxypeptidase A, which is a proteoysis enzyme. As a result, the inner surface of the column filler is covered by glycyl-phenylalanyl phenyl-alanine acting as a hydrophobic ligand, while the outer surface of the filler is covered with hydrophilic glycyl-glyceryl propyl group.

In the process of the '145 reference, on the other hand, a porous silica body infiltrated with aminopropyl group is used as a starting material, and hydrophobic group is introduced by amide bonding by causing a reaction of octanoyl-chloride under presence of triethylamine. After this, acyl group on the outer surface of the silica filler is subjected to hydrolysis reaction, and amino group on the outer surface is made hydrophilic by causing a reaction with glycidol.

On the other hand, the column filler disclosed in the foregoing '159 or '145 reference has a drawback in that, because of use of enzyme reaction, the construction of the column filler becomes complex and the property of the obtained column filler tends to vary variously.

In the conventional liquid chromatograph of the foregoing references, there exists another drawback, associated with the large volumetric capacity of the condensation column 40, in that the sample solution supplied thereto may be unwantedly diluted in the column 40, rather than being concentrated. When this occurs, the sensitivity of detection decreases. It should be noted that the condensation column 40 generally has a volumetric capacity exceeding 200 μl. This problem of deteriorated sensitivity of detection becomes particularly acute for those apparatuses designed for using small amount of sample solution.

Conventionally, it has been known that a better result is obtained when a micro-column having an inner diameter of less than 1 mm is used for the separation column 16, in place of a semi-micro-column that has an inner diameter of 1–2 mm. In fact, liquid chromatography analysis using a micro-column is described in various references such as Scott, R. P. and Kucera, P. J., *J. Chromatogr.*, 125 (1978), pp.271, Tsuda, T. and Novotny, M., *Anal. Chem.* 50 (1978), pp.632, Ishii, D. et al., *J. Chyromatogr.*, 124 (1977), pp.157, and Novotny, M., *Anal. Chem.* 60 (1988) 500A. These references generally stress the advantage of: (1) having a large theoretical number of stages, (2) improved response obtained, when a concentration-sensitive detector is used, due to the concentrating effect, (3) easiness for connecting the liquid chromatograph to other apparatuses that require removal of solvents such as mass spectrometer, and (4) reduced consumption of the solvents.

In spite of these various promising perspectives, practical use of the micro-column liquid chromatograph has not been successful so far, probably due to the instability in the flow rate control and the poor column stability. It should be noted that the stability of the isocratic is essential in the flow rate mode for managing the retention time. Further, such micro-column liquid chromatographs generally have a very basic problem of discrepancy between the volume of the prepared sample solution, typically in the order of several ten micro-litters to several hundred micro-litters, and the volume of the injected sample solution in the liquid chromatograph, which is typically in the order of several micro-litters. When the concentration level of the chemical substance to be analyzed is extremely low in the sample solution, it is naturally desired to use the entirely of the prepared sample solution for the analysis, while the conventional micro-column liquid chromatographs cannot meet such a demand.

In addition, it should be noted that the flow rate of the sample solution in the column 16 has to be set low, in the order of micro liters per minute when a micro-column is used. This level of flow rate is substantially smaller than those used in a semi-micro-column in which the flow rate is typically set to be about 0.05–0.2 ml/min. With reducing diameter of the column 16, the flow rate of the sample solution therein decreases further. Thus, in the construction of the liquid chromatograph of FIG. 7 where the condensation column 40 having a large diameter is connected directly to the micro-column 16, there inevitably occurs a problem of increased time for conducting the measurement. Thereby, the efficiency of analysis is substantially deteriorated.

SUMMARY OF THE INVENTION

Accordingly, it is a general object of the present invention to provide a novel and useful liquid chromatograph wherein the foregoing problems are eliminated.

Another and more specific object of the present invention is to provide a liquid chromatograph equipped with a mixer that enables substantially complete mixing of solvents even in a very low flow rate of the supplied solvents.

Another object of the present invention is to provide a liquid chromatograph equipped with a sampler for supplying a sample solution to a separation column, wherein the sampler supplies the sample solution to the column substantially completely.

Another object of the present invention is to provide a liquid chromatograph, comprising:

a plurality of pumps for supplying a plurality of solvents;

mixing means supplied with said plurality of solvents from said plurality of pumps for mixing said plurality of solvents;

control means for controlling a mixing ratio of said solvents in said mixing means;

a chromatograph column supplied with said solvents from said mixing means for separating a sample that is carried with said solvents;

flow path control means provided between said mixing means and said chromatograph column for receiving said solvents from said mixing means and further with said sample, said flow path control means supplying said sample together with said solvents to said chromatograph column; and detection means supplied with said sample separated by said column, for detecting said sample supplied thereto;

said mixing means comprising a mixing chamber and a porous medium accommodated in said mixing chamber, said porous medium extending between a first end for receiving said solvents from said pumps and a second end for supplying said solvents to said flow path control means and having a size and shape in conformity with a size and shape of said mixing chamber such that no substantial gap is formed between an outer surface of said porous medium and an inner surface of said mixing chamber.

According to the present invention, the mixing of the solvents occurs in the porous medium. Thereby, no substantial dead space is formed between the porous medium and the mixing chamber, and the solvents supplied to the mixing chamber are mixed more or less completely as they pass through the porous medium from the first end to the second end. Thereby, an exact control of composition of the solvents is achieved when the liquid chromatograph is employed for a gradient elution in which the composition of the solvent is controlled according to a program curve.

Another object of the present invention is to provide a liquid chromatograph, comprising:

a plurality of pumps for supplying a plurality of solvents;

mixing means supplied with said plurality of solvents from said plurality of pumps for mixing said plurality of solvents;

control means for controlling a mixing ratio of said solvents in said mixing means;

a chromatograph column supplied with said solvents from said mixing means for separating a sample that is carried with said solvents;

flow path switching means for switching a path of said solvents, said valve means comprising: first flow path means provided between said mixing means and said chromatograph column for receiving said solvents from said mixing means and further with said sample, said flow path means supplying said sample together with said solvents to said chromatograph column; second flow path means supplied with said sample for supplying said sample to said chromatograph column together with said solvents; third flow path means for selectively causing said second flow path means to communicate with a waste reservoir; and a sample holder supplied with said sample for holding said sample therein;

detection means supplied with said sample separated by said chromatograph column for detecting said sample supplied thereto;

said valve means comprising:

a stationary member carrying thereon a first port connected to said mixing means; a second port connected to a first end of said sample holder; a third port for receiving said sample; a fourth port connected to said waste reservoir; a fifth port connected to a second end of said sample holder; and a sixth port connected to said chromatograph column;

a rotatable valve body defined by a first surface and a second, opposite surface, said rotatable valve being provided rotatably on said stationary member to form a slidable engagement with said stationary member at said first surface, said rotatable valve body being rotatable between a first state and a second state, said rotatable valve body carrying thereon first through sixth flow paths such that, in said first state, said first flow path coincides with said first port, said second flow path coincides with said second port, said third flow path coincides with said third port, said fourth flow path coincides with said fourth port, said fifth flow path coincides with said fifth port and said sixth flow path coincides with said sixth port, and such that, in said second state, said first flow path coincides with said sixth port, said second flow path coincides with said first port, said third flow path coincides with said second port, said fourth flow path coincides with said third port, said fifth flow path coincides with said fourth port and said sixth flow path coincides with said fifth port;

said rotatable valve body carrying, on said second surface, a first groove connecting said first flow path and said sixth flow path, a second groove connecting said second flow path and said third flow path, a third groove connecting said fourth flow path and said fifth flow path; and a seal member provided on said second surface of said rotatable valve body so as to rotate together with said rotatable valve body, said seal member being provided upon said second surface with an intimate contact therewith.

According to the present invention in which the second surface or bottom surface of the valve body carries the passage of fluid in the form of grooves, it is no longer necessary to provide the passage of the fluid in the seal member with tolerance, and the problem of formation of dead space due to the tolerance of the groove on the seal member is successfully eliminated.

Another object of the present invention is to provide a liquid chromatograph, comprising:

a pump for pumping a solvent;

a chromatograph column supplied with said solvent from said pump for separating a sample from said solvent;

first flow path control means disposed between said pump and said chromatograph column, said first flow path control means being supplied with said solvent and further with a sample for supplying said solvent and said sample, supplied to said first flow path control means, together to said chromatograph column;

detection means supplied with said sample from said column after separation, for detecting said sample supplied thereto;

a sample holder mechanism including a plurality of vessels containing a plurality of samples;

sample injection means for selectively collecting a sample from one of said plurality of vessels for supplying said collected sample to said first flow path control means; and second flow path control means for selectively supplying said sample from said detection means, after detection in said detection means, to said sample injection means;

wherein said sample injection means stores said sample supplied from said second flow path control means in one of said vessels in said sample holder mechanism.

According to the present invention, the second flow path control means selectively supplies the sample, after separation in the chromatograph column and analysis in the detection means, to a vessel in the sample holder mechanism, such that the samples after the chromatographic analysis are held in the sample holder mechanism together with the samples yet to be analyzed. Thereby, it is possible to use the samples analyzed for further processes and various purposes, after the chromatographic analysis. As the samples yet to be analyzed and the samples that have already been analyzed are held on the common sample holder mechanism, the liquid chromatograph has a compact size. The first and second flow path control means are easily realized by a six-port valve mechanism having six ports and three fluid passages each connecting two of the six ports. The present invention is particularly useful in the liquid chromatograph having a semi-micro or micro column in which the total flow rate of the solvent and the sample is held at a level of 200 µl/min or less.

Another object of the present invention is to provide a process for analyzing a sample by means of a liquid chromatograph, comprising the steps of:

(a) pulling air into a sample injection tube to form an air gap in said sample injection tube;

(b) pulling an inert liquid into said sample injection tube to form an inert liquid droplet in said sample injection tube, said inert liquid having a composition such that said inert liquid does not affect the result of a liquid chromatographic analysis in said liquid chromatograph;

said steps (a) and (b) being conducted at least once;

(c) pulling a sample solution into said sample injection tube, after said step (b), to form a sample liquid droplet in said sample injection tube; and (d) supplying said sample liquid droplet and said inert liquid droplet to a chromatographic column for chromatographic analysis of said sample liquid droplet;

said step (d) being conducted such that said sample liquid droplet is supplied to said chromatographic column, followed by one or more of said inert liquid droplets.

Another object of the present invention is to provide a liquid chromatograph, comprising:

a chromatographic column supplied with a sample solution together with a solvent for separating said sample solution;

detection means supplied with said sample solution from said chromatographic column for detecting said sample solution supplied thereto;

a piping system connected to said chromatographic column for supplying said sample solution to said chromatographic column;

a first vessel for holding said sample solution;

a second vessel for holding an inert solution that does not affect a detection of said sample solution;

sample injection means for pulling said sample solution from said first vessel and for holding said sample solution in the form of a sample liquid droplet, said sample injection means further pulling said inert solution from said second vessel and holding said inert solution in the form of an inert liquid droplet, said sample injection means injecting said sample liquid droplet and said inert liquid droplet to said piping system; and injection control means for controlling said sample injection means such that said sample injection means holds one or more of said inert liquid droplets separated from each other by one or more air gaps and such that said sample injection means pulls said sample solution after said one or more inert liquid droplets are held in said sample injection means, said injection control means further controlling said sample injection means such that said sample liquid droplet is injected to said piping system, followed by said one or more inert liquid droplets.

According to the present invention, the sample liquid left on a wall of a tube extending to the chromatographic column is grabbed and transported to the column, together with one or more of the inert liquid droplets that follow the sample liquid droplet. Thereby, substantially entire sample solution is supplied to the chromatographic column for analysis, and the precision as well as the reliability of the result of analysis are improved substantially.

Another object of the present invention is to provide a dual-column chromatograph having a condensation column for concentrating a sample solution prior to a secondary chromatographic analysis, wherein the volumetric capacity of the condensation column is set small enough for use in combination with a semi-micro or micro separation column.

Another object of the present invention is to provide a liquid chromatograph, comprising:

a pump for pumping a solvent:

a separation column supplied with a sample solution for separating a sample contained therein;

detection means for detecting said sample separated by said separation column;

sample injection means supplied with said solvent from said pump for injecting a sample to said solvent to produce a sample solution, said sample solution containing said sample in said solvent; and a condensation column provided between said injection means and said separation column, said condensation column being supplied with said sample solution from said sample injection means for concentrating said sample to produce a concentrated sample solution, said condensation column supplying said concentrated sample solution to said separation column as said sample solution;

wherein said condensation column has a volumetric capacity less than 2 milliliters; and wherein said condensation column is filled with a column filler of a porous medium covered by a silicone polymer having a Si—R bond and a Si—R' bond, wherein R represents a hydrophobic group and R' represents a hydrophilic group.

According to the present invention that uses a column having a small volumetric capacity for the condensation column, one can eliminate the problem of unwanted dilution of the sample solution in the condensation column, and it is possible to obtain an accurate analysis as a result of condensation of the sample solution. By using a porous medium covered by a silicone polymer having an Si—R bond or Si—R' bond, it is possible to eliminate the adsorption of protein on the outer surface of the column filler, and a reliable condensation of the sample solution can be achieved. It should be noted that the present invention does not rely upon enzyme reaction.

Another object of the present invention is to provide a multi-column liquid chromatograph, comprising: at least two pumps for pumping respective solvents;

a separation column for separating a sample transferred from a previous column;

detection means for detecting said sample separated by said separation column;

sample injection means supplied with said solvent from said pump for injecting a sample to said solvent to produce a sample solution, said sample solution containing said sample in said solvent; and a plurality of precolumns provided between said injection means and said separation column for concentrating a sample solution supplied thereto;

wherein at least one of said precolumns has a larger diameter than that of a separation column.

According to the present invention, it is possible to achieve a stable and effective condensation of the sample solution before the separation of the sample is achieved in the separation column. As a result, a high sensitivity analysis is possible for a dilute sample solution. By the use of precolumn(s), it is possible to prevent the decrease of flow rate of the mobile phase in the first stage separation, and the problem of increased time for the analysis is effectively eliminated. Associated with this, the present invention is particularly advantageous for those liquid chromatographs that use a semi-micro or micro column for the separation column. It should be noted that the sensitivity of detection is maximized in such a semi-micro or micro column liquid chromatograph due to the decreased flow rate of the sample solution in the second stage separation. Further, such a decreased flow rate in the separation column is advantageous in view point of supplying the sample solution further to other analytical apparatuses such as a mass spectrometer. In addition, such a reduced flow rate of the sample solution is preferable in view of reduced consumption of the solvents.

Other objects and further features of the present invention will become apparent from the following detailed description when read in conjunction with the attached drawings.

BRIEF DESCRIPTION OF THE DRAWINGS

FIGS. 2A–2D are diagrams showing the operational characteristics of the liquid chromatograph of FIG. 1;

FIG. 14 is a diagram showing the liquid chromatograph of FIG. 13 in a different state;

FIGS. 29A and 29B are diagrams showing a still other process of forming hydrophilic and hydrophobic sites on a silicone polymer film that covers the surface of a filler used in the liquid chromatograph of the sixth embodiment;

FIGS. 30A–30D are diagrams showing a still other process of forming hydrophilic and hydrophobic sites on a silicone polymer film that covers the surface of a filler used in the liquid chromatograph of the sixth embodiment;

DETAILED DESCRIPTION OF THE PREFERRED EMBODIMENTS

Figure 8:
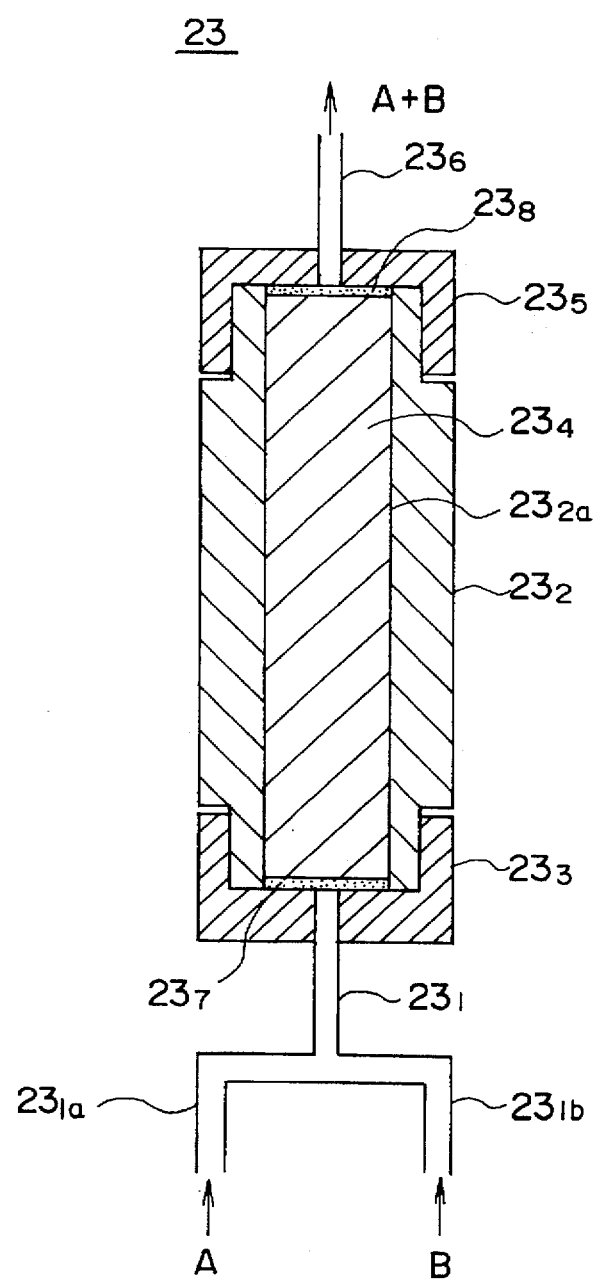
FIG. 8 is a diagram showing the construction of a mixer for use in a liquid chromatograph according to a first embodiment of the present invention.

FIG. 8 shows a first embodiment of the present invention. More specifically, FIG. 8 shows a mixer 23 for use in the liquid chromatograph of FIG. 1 in a cross sectional view.

Figure 6:
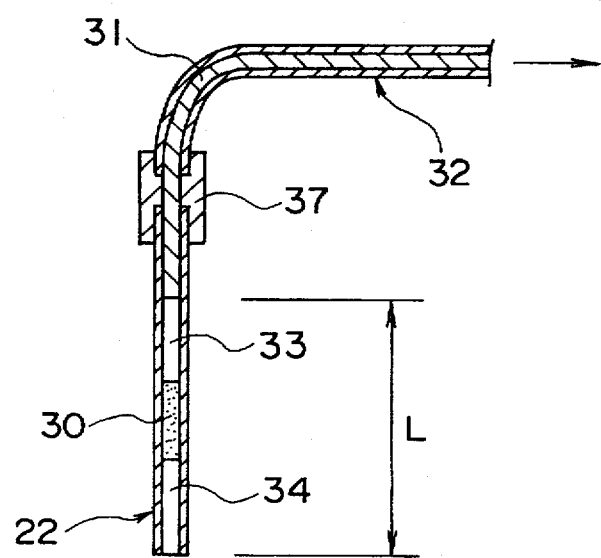
FIG. 6 is a diagram showing the construction of a sample injection tube used in the liquid chromatograph of FIG. 1.

Referring to FIG. 6, the mixer 23 is formed of a cylindrical vessel $23_2$ of stainless steel or a plastic material wherein the vessel $23_2$ is formed with a corresponding cylindrical mixing chamber $23_{2a}$ therein. Typically, the mixing chamber $23_{2a}$ has an inner diameter of 1.0–5.0 mm and extends for a length of 3–10 cm.

It should be noted that the mixing chamber $23_{2a}$ is filled with a porous resin body $23_4$ having a cylindrical shape corresponding to the cylindrical mixing chamber $23_{2a}$, wherein it will be noted that the resin body $23_4$ has an outer diameter of 1.0–5.0 mm and a length of 3–10 cm respectively in correspondence to the inner diameter and length of the chamber $23_{2a}$. For example, the resin body $23_4$ has an outer diameter of 1.5 mm when the mixing chamber $23_{2a}$ has an inner diameter of 1.5 mm. The resin body $23_4$ may be formed of a porous fluorocarbon resin, and is conveniently obtained by stamping a porous slab of fluorocarbon with a predetermined diameter.

Figure 9:
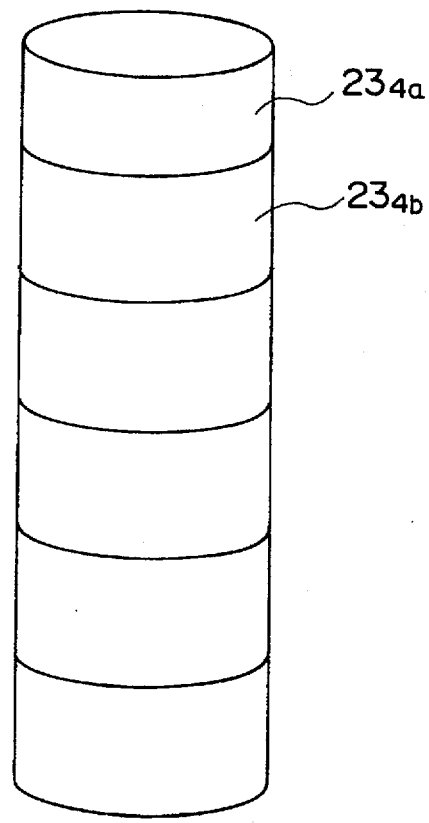
FIG. 9 is a diagram showing the construction of a porous medium used in the mixer of FIG. 8 for mixing a sample solution without formation of a dead volume.

As shown in FIG. 9, the mixing chamber $23_{2a}$ is filled with resin disks $23_{4a}$, $23_{4b}$, . . . thus stamped, wherein the resin disks $23_{4a}$, $23_{4b}$, . . . are stacked with a predetermined number to form the foregoing resin body $23_4$ of a predetermined length. By filling the mixing chamber $23_{2a}$ by such resin disks, it is possible to eliminate the dead space substantially completely from the mixing chamber $23_{2a}$.

Referring to FIG. 8 again, a pair of filters $23_7$ and $23_8$ of sintered stainless steel are disposed at both ends of the resin body $24_4$, and caps $23_3$ and $23_5$ both of stainless steel are provided upon respective ends of the stainless steel vessel $23_2$. It should be noted that the caps $23_3$ and $23_5$ carry respective ports $23_1$ and $23_6$ and are screwed upon the vessel $23_2$ at the ends of the vessel $23_2$. It should be noted that port $23_1$ has branched ends $23_{1a}$ and $23_{1b}$, wherein the solvent A is supplied to the end $23_{1a}$ by means of the pump 11A. Similarly, the solvent B is supplied to the end $23_{1b}$ by means of the pump 11B. The solvents A and B thus supplied are mixed with each other as they flow through the porous resin body $23_4$ and is exhausted from the outlet port $23_6$.

Figure 10:
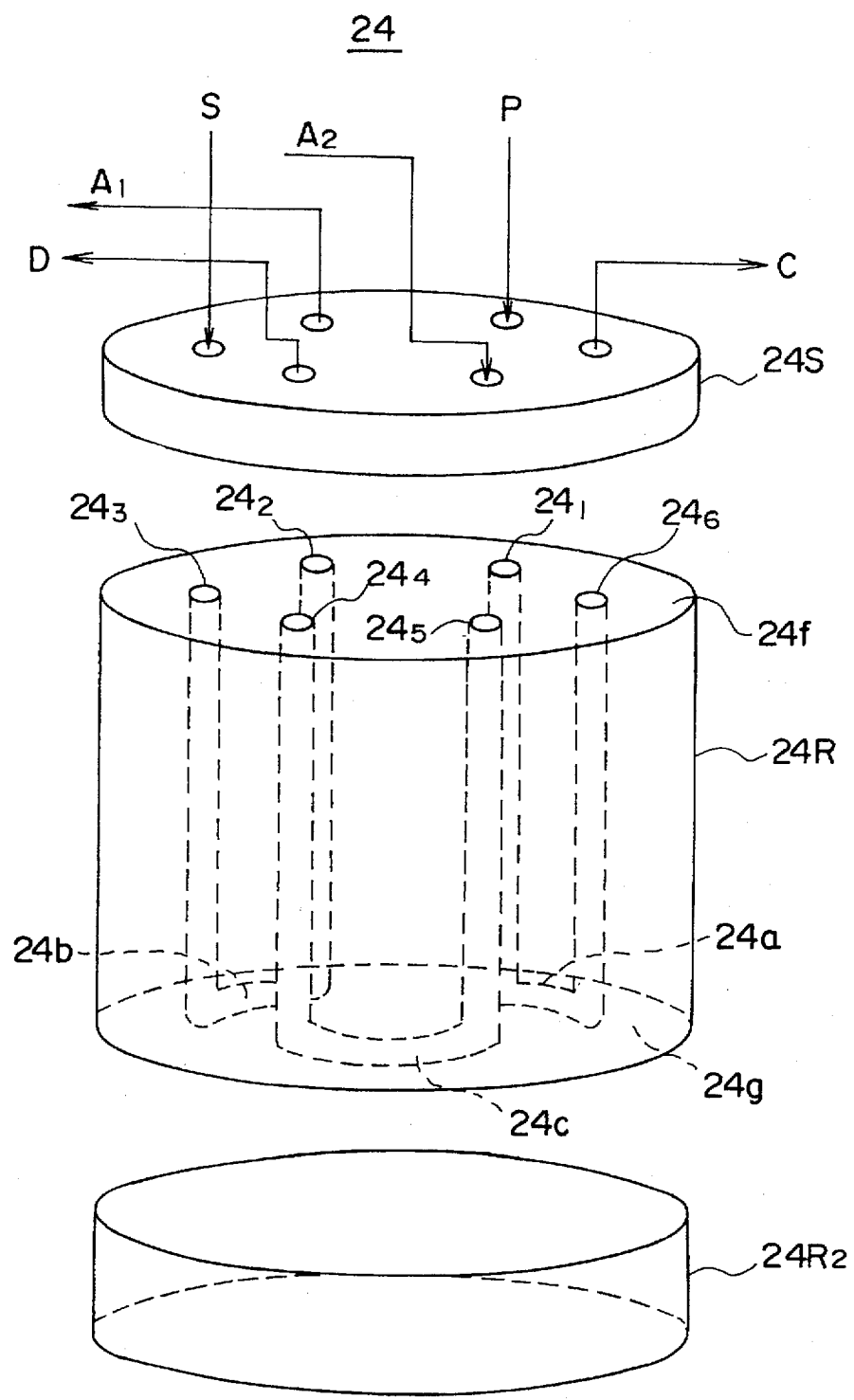
FIG. 10 is a diagram showing the construction of a six-port valve for use in a liquid chromatograph according to a second embodiment of the present invention in an exploded view.

Next, a second embodiment of the present invention will be described with reference to FIG. 10, wherein FIG. 10 shows the construction of a six-port valve 24 that is used in the liquid chromatograph of FIG. 1 in place of the six-port valve 14.

Figure 4:
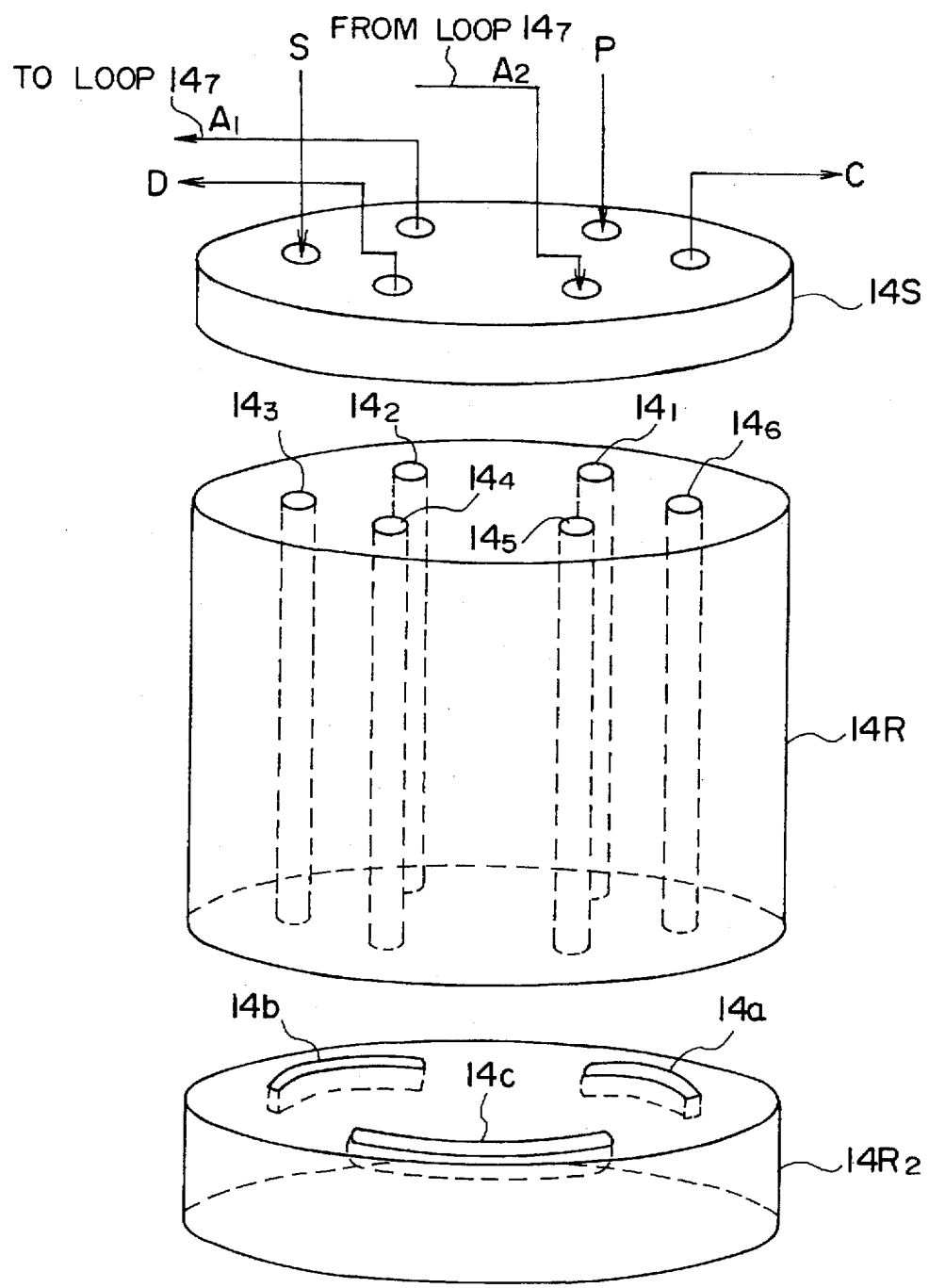
FIG. 4 is a diagram showing the conventional construction of the six-port valve used in the liquid chromatograph of FIG. 1.

Referring to FIG. 10, the six-port valve 24 includes a stationary cap 24S substantially identical to the stationary cap 14 of FIG. 4, and a rotary valve body 24R engages with the foregoing stationary cap 24S. More specifically, the rotary valve body 24R has a cylindrical shape defined by a first end surface 24f and a second, opposite end surface 24g and is mounted upon the stationary cap 24S such that the end surface 24f establishes a slidable, yet intimate engagement with the cap 24S. As a result, a seal is formed between the rotary valve body 24R and the stationary cap 24S. Further, there is provided another cap $24R_2$ on the end surface $24_g$ of the rotary valve body 24R.

In the rotary valve body 24R, there are provided six straight fluid passages $24_1$–$24_6$ extending from the end surface 24f to the end surface 24g similarly to the rotary valve body 14R of FIG. 4. On the other hand, it should be noted that the rotary valve body 24R of FIG. 10 carries grooves 24a–24c on the end surface 24g as the passage of the fluid. As indicated in FIG. 10, the groove 24a connects the passages $24_1$ and $24_6$, the groove 24b connects the passages $24_2$ and $24_3$, and the groove 24c connects the passages $24_4$ and $24_5$. Associated with the formation of the grooves 24a–24c on the rotary valve body 24R, no groove is provided on the cap $24R_2$.

Figure 5:
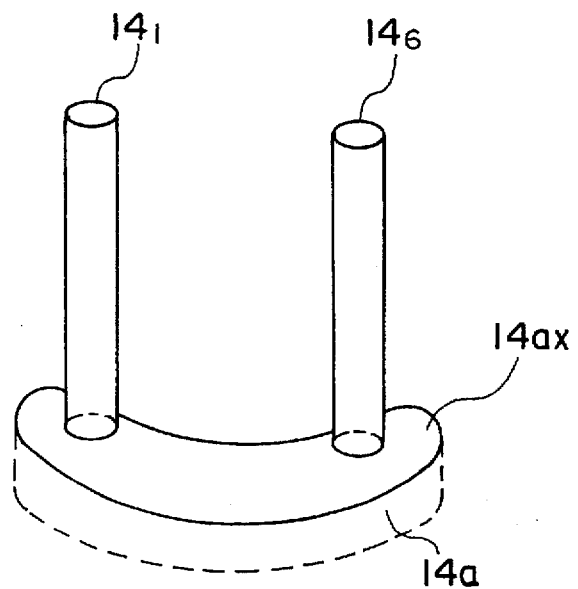
FIG. 5 is a diagram showing a part of the liquid chromatograph of FIG. 4 in an enlarged scale.

The rotary valve body 24R may be formed of a ceramic or resin. When a ceramic is used for the valve body 24R, the grooves 24a–24c may be formed on a green body by machining, simultaneously to the formation of the fluid passages $24_1$–$24_6$. When the valve body 24R is formed of a resin such as PEEK (polyether etherketone), the grooves 24a–24c may be formed either simultaneously to the molding of the valve body 24R or by machining the end surface 24g of the valve body 24R thus formed. In any of these processes, it should be noted that the grooves 24a–24c are formed with an exact alignment with the fluid passages $24_1$–$24_6$. In other words, there is no necessity to form the fluid passages $24_1$–$24_6$ excessively large for securing tolerance, contrary to the conventional case shown in FIG. 5, and the formation of dead space is positively eliminated. Associated with this, unwanted dwelling of the sample solution in the dead space is eliminated, and the accuracy of the chromatographic analysis is improved substantially.

In the six-port valve of FIG. 10, it should be noted that the cap $24R_2$ may be a mere disk that is fixed firmly upon the rotary valve body 24R by a suitable means such as screws. Of course, there is formed a tight seal at the interface between the valve body 24R and the disk $24_2$.

Figure 1:
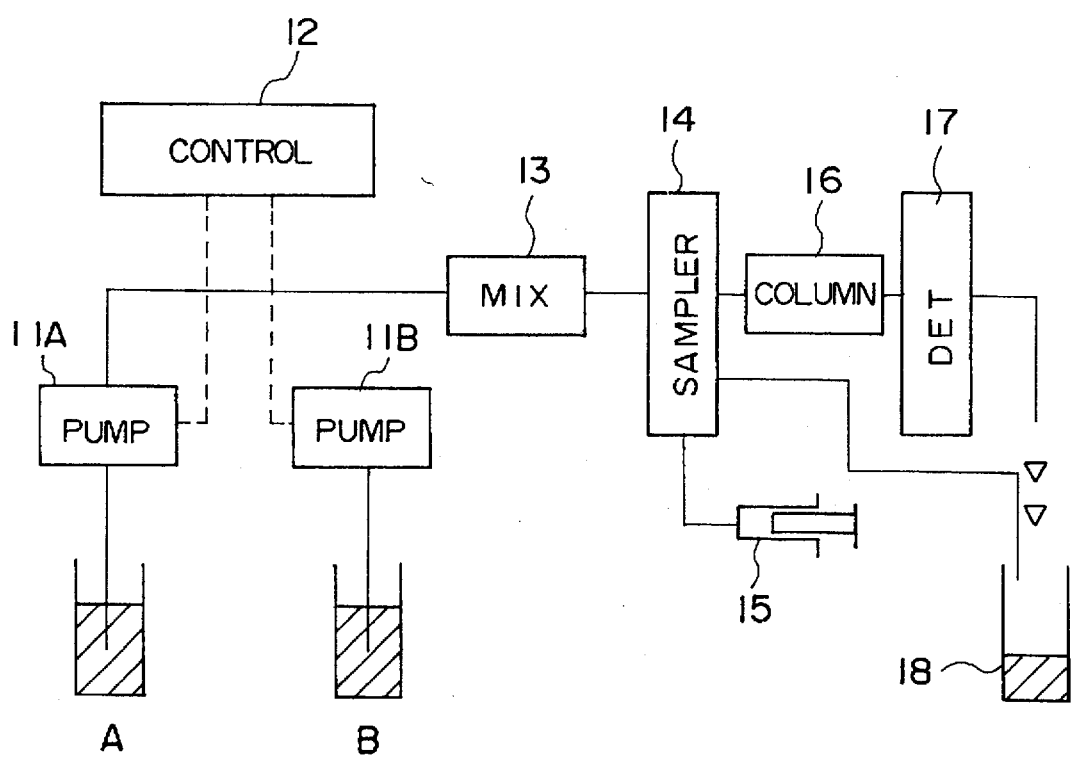
FIG. 1 is a diagram showing the construction of a conventional liquid chromatograph.

As the construction of the piping system as well as the operation of the six-port valve 24 in the liquid chromatograph of FIG. 1 are substantially identical with those described with reference to the prior art, further description thereof will be omitted.

Figure 11:
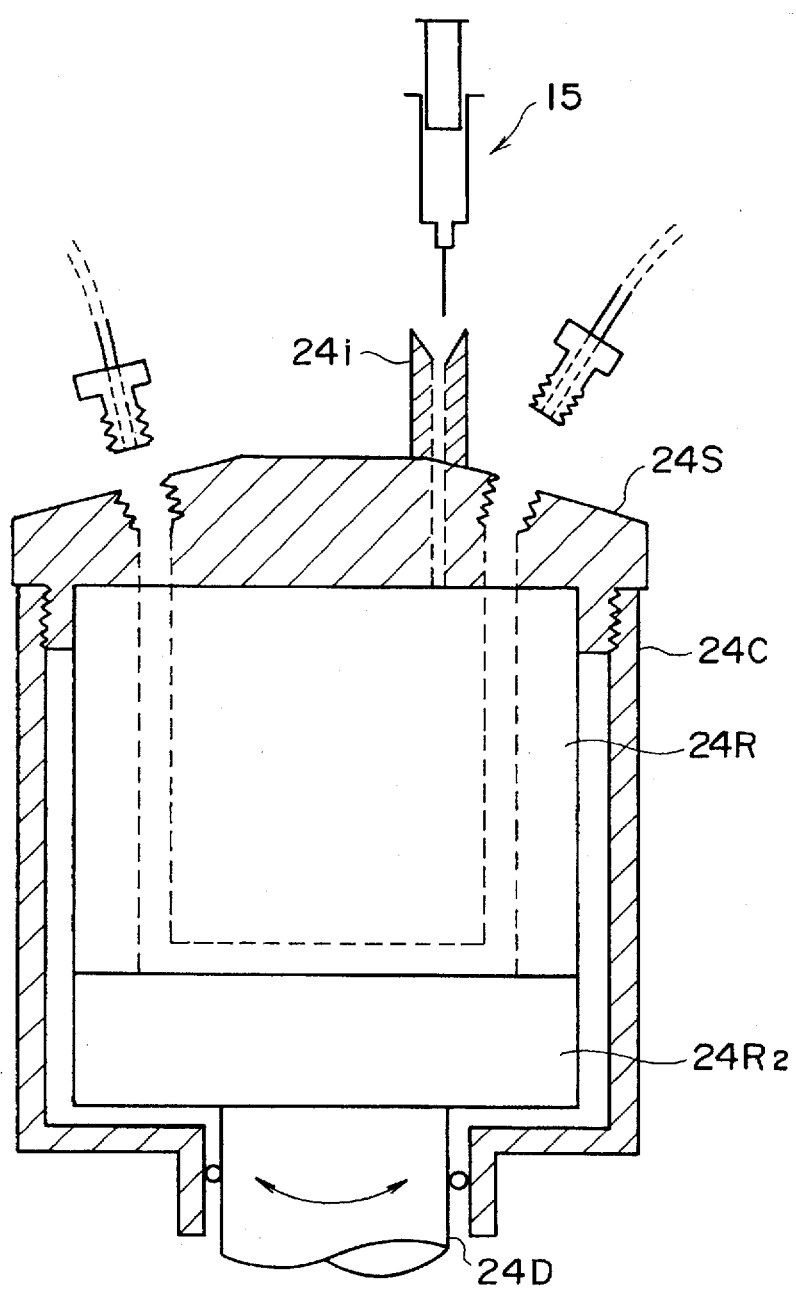
FIG. 11 is a diagram showing the six-port valve of FIG. 10 in an elevational cross sectional view.

FIG. 11 shows a construction for mounting the six-port valve of FIG. 10 on the liquid chromatograph of FIG. 1.

Referring to FIG. 11, it should be noted that the valve bodies 24R and $24R_2$ are accommodated together in a casing 24C of stainless steel, and the stationary cap 24S is fitted upon the casing 24C by screwing. Further, the valve bodies 24R and $24R_2$ are mounted upon a rod 24D so as to be rotated integrally with the rod 24D. Further, the stationary cap 24S includes various threaded holes for receiving insertion of various pipings shown in FIG. 1. Further, there is provided a guide member 24$i$ on the cap 24S for receiving the sample injection tube of the syringe 15 that holds the sample solution.

Figure 12:
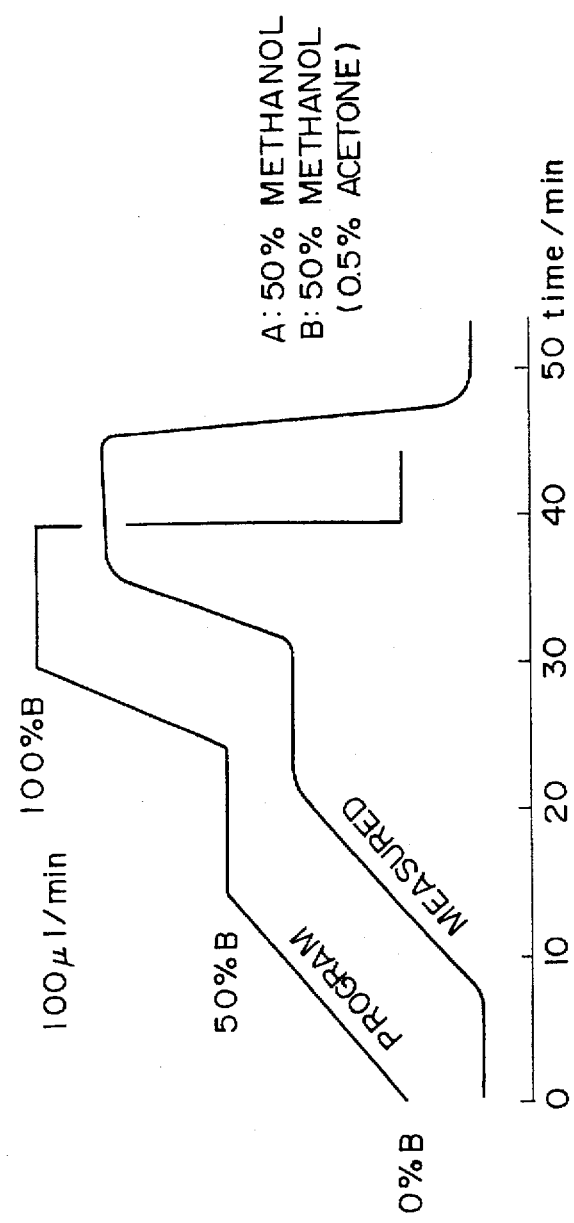
FIG. 12 is a diagram showing the operational characteristics of the liquid chromatograph in which the mixer of FIG. 8 and the six-port valve of FIG. 10 are used.

FIG. 12 shows the response for switching the solvents for a case in which the combination of the mixer 23 of FIG. 8 and the six-port valve 24 of FIG. 10 is used in the liquid chromatograph of FIG. 1. In FIG. 12, it should be noted that the experimental conditions are set substantially the same as in the case of FIGS. 2A–2D, except that the total flow rate is set to 100 µl/min. From FIG. 12, it will be noted that the liquid chromatograph of the present invention can provide a sufficient response with respect to the switching of the solvent or sudden change in the composition of the solvent, even in the case of such a small total flow rate.

Next, a third embodiment of the present invention will be described with reference to FIG. 13, wherein those parts described previously are designated by the same reference numerals and the description thereof will be omitted.

Figure 13:
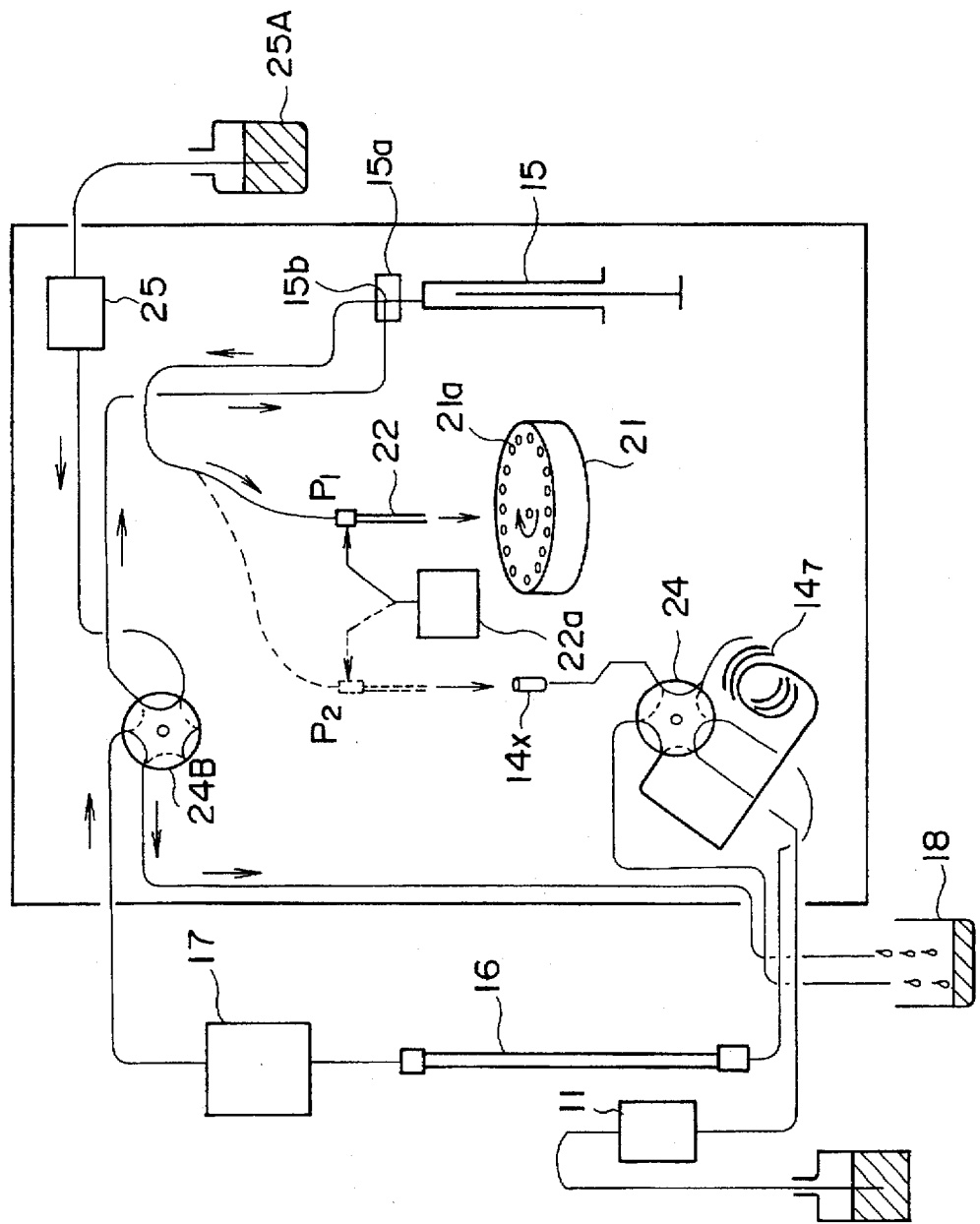
FIG. 13 is a diagram showing the construction of a liquid chromatograph according to a third embodiment of the present invention.

Referring to FIG. 13, the liquid chromatograph includes a sample holder 21 including a plurality of sample vials 21$a$ for holding the samples to be analyzed. Each of the vials 21$a$ has a volumetric capacity of about 200 µl, and there is provided a robot 22$a$ for carrying the sample injection needle 22 movably between a position $P_1$ and a position $P_2$ such that the sample injection needle 22 is inserted into one of the vials 21$a$ when in the position $P_1$. The sample injection needle 22 is connected to the syringe 15 by means of a tube, and the syringe 15 picks up the sample in the vial 21$a$ via the needle 22. It should be noted that the sample loop $14_7$ is formed with an injection port 14$x$ adapted for receiving the needle 22, and the sample held in the syringe 15 is injected to the loop $14_7$ via the injection port 14$x$ upon movement of the needle 22 to the position $P_2$ corresponding to the injection port 14$x$.

In the illustrated liquid chromatograph, there is further provided a second six-port valve 24B at the outlet of the detector 17, wherein the second six-port valve 24B supplies the sample, ejected from the detector 17 after analysis, selectively either to the waste reservoir 18 or the sample injection needle 22. In the state of FIG. 13, the sample ejected from the detector 17 after analysis is supplied to the waste reservoir 18 along a feed path indicated by arrow. When feeding the ejected sample to the sample injection needle 22, on the other hand, the sample is supplied to the needle 22 via a flow path 15$b$ provided in a T-joint 15$a$. It should be noted that the flow path 15$b$ in the T-joint 15$a$ supplies any of the sample fed from the syringe 15 and the sample from the valve 24B to the sample injection needle 22.

It should be noted that the illustrated apparatus includes a vessel 25A for holding a rinsing liquid used for cleaning the column 16 as well as the piping system cooperating therewith, such that the rinsing liquid in the vessel 25A is supplied to the foregoing six-port valve 24B by means of a pump 25. In the illustrated state of FIG. 13, the rinsing liquid is supplied to the needle 22 via the joint 15$a$ for cleaning the needle 22. When cleaning the needle 22, the robot 22$a$ moves the needle 22 to a cleaning position $P_3$ different from any of the foregoing positions $P_1$ and $P_2$.

FIG. 14 shows the state in which the six-port valve 24B has rotated with respect to the state of FIG. 13. In the state of FIG. 14, the sample ejected from the detector 17 passes through the valve 24B along a path indicated by an arrow and supplied to the sample injection needle 22 via the flow path 15$b$ in the T-joint 15$a$. On the other hand, the rinsing liquid from the vessel 25A is blocked at the valve 24B. Thus, by moving the needle 22 to a suitable position corresponding to a selected vial 22$a$ of the sample holder 21 in this state, the sample ejected from the detector 17 is collected in the foregoing vial 21$a$.

In the case of using a semi-micro column having a column inner diameter of 1.0–2.0 mm for the separation column 16, it should be noted that the total flow rate of the solvent is at best 50–200 µl/min. Thus, the dilution of the ejected sample by the solvent does not cause any problem at all, and the sample thus collected is successfully stored in the vial 21$a$ typically having a volumetric capacity of several hundred micro-litters, which is sufficient for accommodating the collected sample.

Figure 15A:
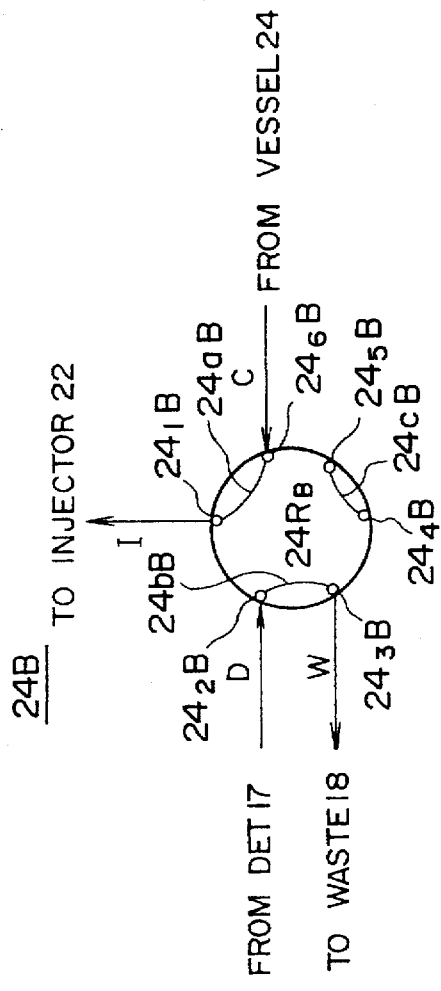
FIGS. 15A and 15B are diagrams showing the state of a valve used for recovering a sample solution.
Figure 15B:
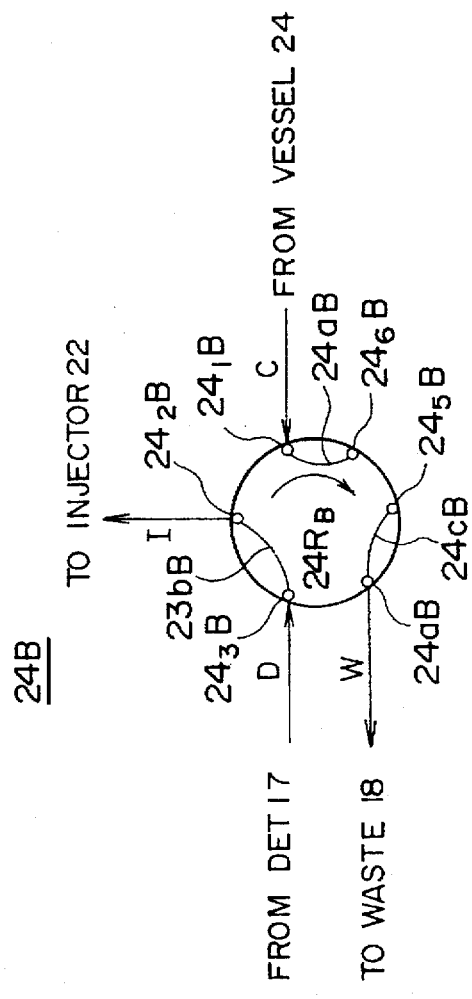

FIGS. 15A and 15B show the switching of flow path of the sample ejected from the detector 17 by the six-port valve 24B.

Referring to FIG. 15A, the six-port valve 24B includes a rotatable valve body 23R that carries thereon straight passages $24_1B$–$24_6B$ as well as passages 24$a$B–24$c$B connecting the passages $24_1B$–$24_6B$. Here, it should be noted that the passage 24$a$B connects the passages $24_1B$ and $24_6B$, the passage 24$b$B connects the passages $24_2B$ and $24_3B$, and the passage 23$c$ connects the passages $23_5$ and $23_6$. In the state of FIG. 15A, the passage $24_1B$ matches a port I that is connected to the sample injection needle 22 via the T-joint 15$a$, the passage $24_2B$ matches a port D connected to the outlet of the detector 17, and the passage $24_3B$ matches a port W connected to the waste reservoir 18. On the other hand, the passage $24_6B$ matches a port C connected to the vessel 25A that holds the rinsing liquid, while the passages $24_5B$ and $24_{6B}$ are connected nowhere. In other words, the sample ejected from the detector 17 is supplied to the waste reservoir 18 after passing through the passage 23$b$ and the port W. On the other hand, the cleaning solution in the vessel 25A is connected to the sample injection needle 22 via the passage 24$a$B.

In the state of FIG. 15B, on the other hand, the valve body 24RB is rotated in the direction of the arrow, and the port I is connected to the detector 17 via the passages $24_2B$, 24$b$B and $24_3B$. Further, the port C is connected to the passages $24_1B$, 24$a$B and $24_6B$. On the other hand, the passage $24_6B$ is connected nowhere. Thus, the rinsing liquid from the vessel 25A is blocked at the passage $24_6B$. In the state of FIG. 15B, the port W connected to the waste reservoir 18 is now connected to the passage $24_5B$ via the passage 23$c$B. However, no ejection of the sample to the waste reservoir 18 occurs in this state, because of the absence of the port connected to the passage $24_5B$.

Figure 16:
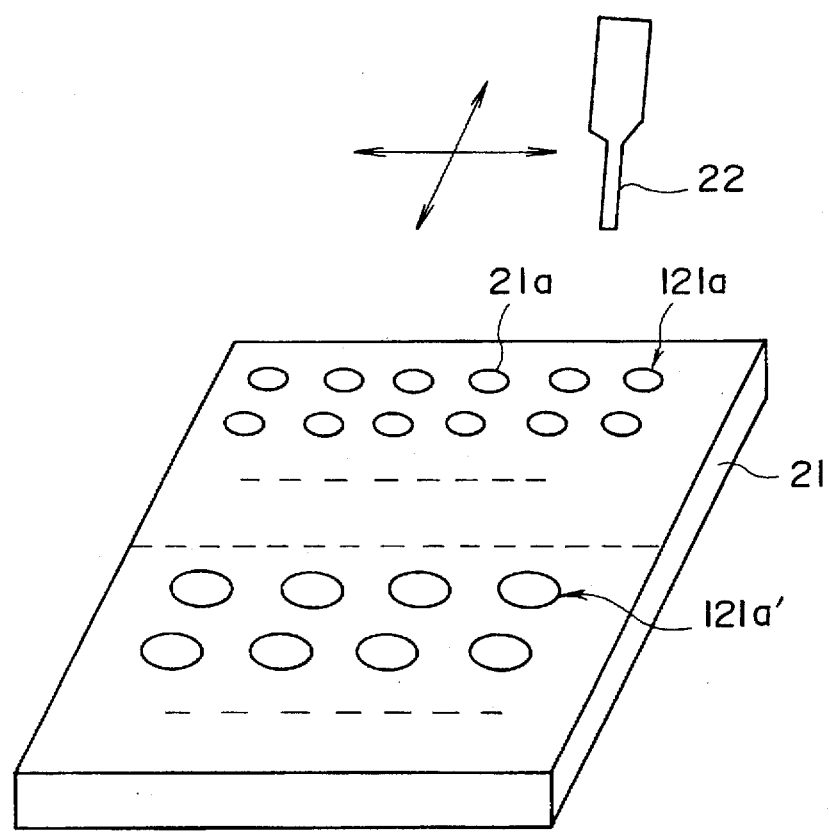
FIG. 16 is a diagram showing a sample holder used in the liquid chromatograph of FIG. 13.

FIG. 16 shows a modification of the third embodiment.

In the construction of FIG. 16, it should be noted that the sample holder 21 is formed in a rectangular shape, and the vials 21a are formed on the sample holder 21 in rows and columns. Thereby, two regions 121a and 121a' are formed on the sample holder 21 such that the vials in the region 121a have a size different from the vials in the region 121a'. For example, the vials in the region 121a' have a larger volumetric capacity as compared with the vials in the region 121a. Thereby, the storage of the recovered sample is possible even in the case the sample ejected from the detector 17 has an increased volume due to dilution by solvents.

Figure 17:
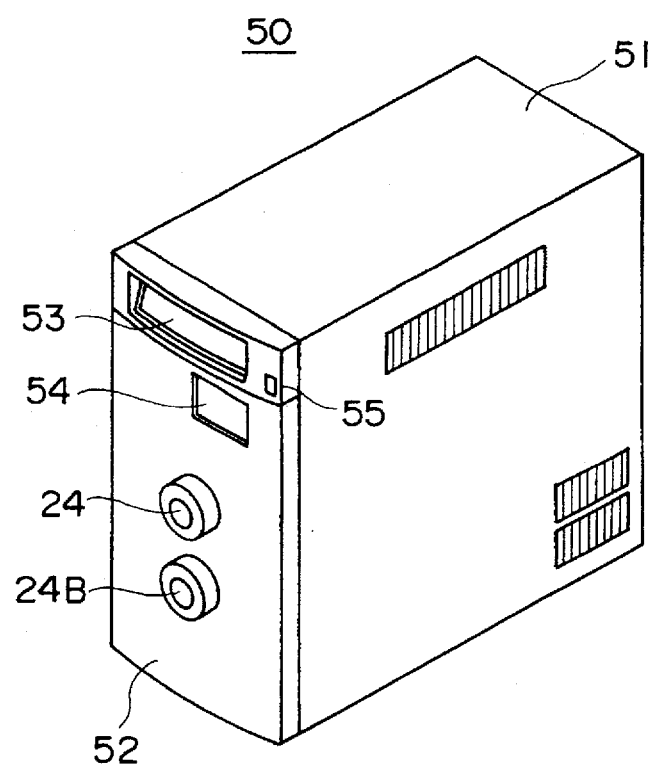
FIG. 17 is a diagram showing a valve unit for use in a liquid chromatograph according to a fourth embodiment of the present invention.

Next, a fourth embodiment of the present invention will be described with reference to FIG. 17 showing a valve unit 50 for use in the liquid chromatograph of FIGS. 13 and 14.

It should be noted that the liquid chromatograph of FIGS. 13 and 14 uses two six-port valves 14 and 23. The valve unit of FIG. 17 of the present invention thus assembles the valves 14 and 23 in the form of a single valve unit 50.

Referring to FIG. 17 showing the valve unit 50 in a perspective view, the valve unit 50 has a case 51 that includes a front panel 52 on which a display device 53, a key pad 54 and a power switch 55 are provided.

Figure 18:
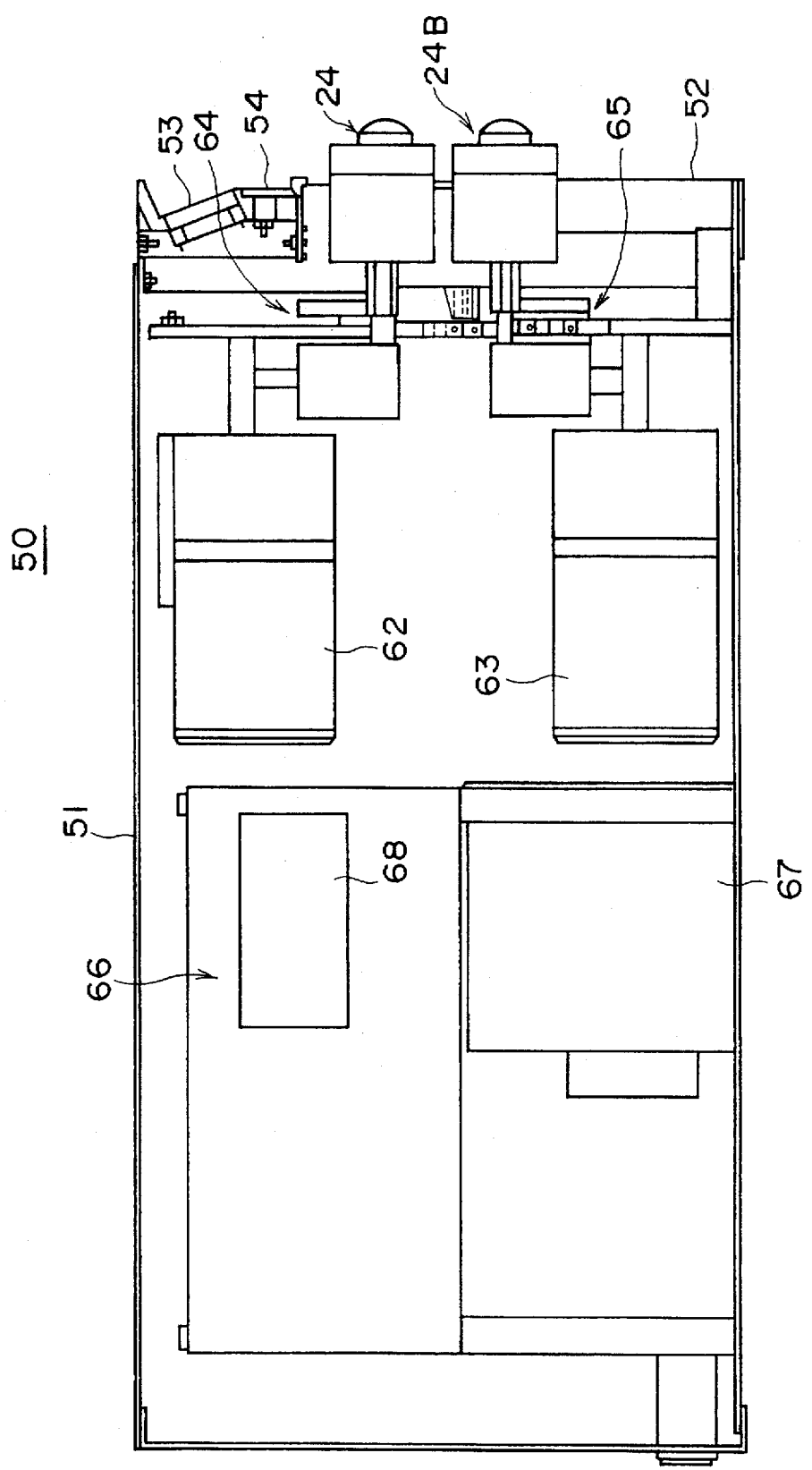
FIG. 18 is a diagram showing the interior of the valve unit of FIG. 17.

FIG. 18 shows the interior of the case 51.

Referring to FIG. 18, it will be noted that the case 51 includes a first valve actuation motor 62 for actuating the six-port valve 14 and a second valve actuation motor 63 for actuating the six-port valve 24B, wherein the motor 62 actuates the valve 14 via a reduction mechanism 64. Similarly, the motor 63 actuates the valve 24B via a reduction mechanism 65. In order to drive the motors 62 and 63, there is provided a printed circuit board 66 in the case 51 of the valve unit 50, wherein the printed circuit board 66 carries thereon a microcomputer 68 for controlling the motors 62 and 63 and a switching regulator 67.

The display device 53 on the front panel 52 may be a liquid crystal display and represents the status of the valve unit 50 including the content inputted via the key pad 54. It should be noted that the key pad 54 is used for various settings of the valve unit 50 as well as for inputting programs and data to the microcomputer 68. The power switch 55 is used for turning on and turning off the electric power of various electronic components inside the valve unit 50. The switching regulator 67, in turn, acts as a stabilized power supply by causing a high frequency switching of the input electric power.

Figure 3A:
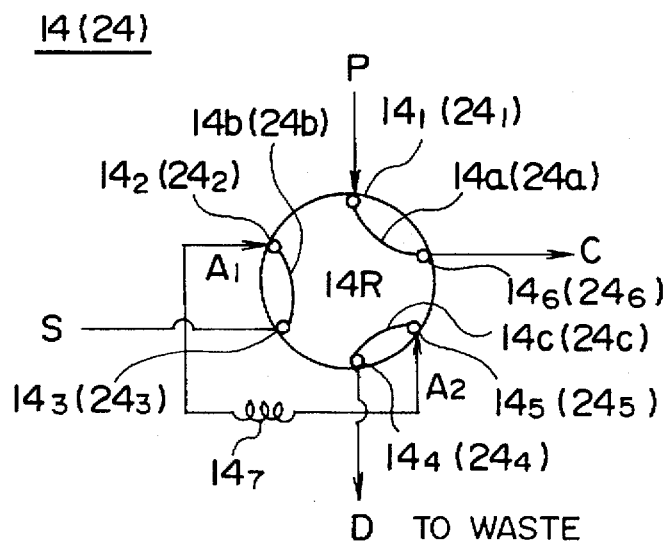
FIGS. 3A and 3B are diagrams showing the operation of a six-port valve used in the liquid chromatograph of FIG. 1.
Figure 3B:
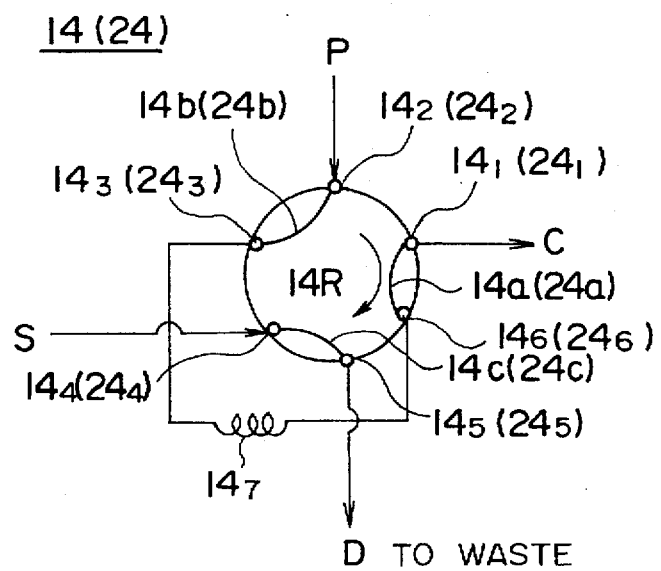

It should be noted that the motor 62 for driving the valve 14 may be a d.c. motor and has an output shaft connected to the valve 14 via the reduction mechanism 53 described already. Similarly, the motor 64 may be a d.c. motor and has an output shaft connected to the valve 24B by way of the reduction mechanism 65. As already noted, the motors 62 and 63 are driven under control of the microcomputer 68, and the switching of the flow path described previously with reference to FIGS. 3A and 3B for the valve 14 or with reference to FIGS. 15A and 15B for the valve 24B is achieved.

Because of the fact that the microcomputer 68 for controlling the motors 62 and 63 are provided in the form of integral unit 50, there is no need to provide an external controller outside the unit 50. Associated with this, it is possible to eliminate various wirings and electric connections associated with the use of external controllers.

Next, a fifth embodiment of the present invention will be described with reference to FIGS. 19 and 20 corresponding to FIGS. 13 and 14 described previously. Thus, those parts described already with reference to FIGS. 13 and 14 are designated by the same reference numerals and the description thereof will be omitted.

Figure 19:
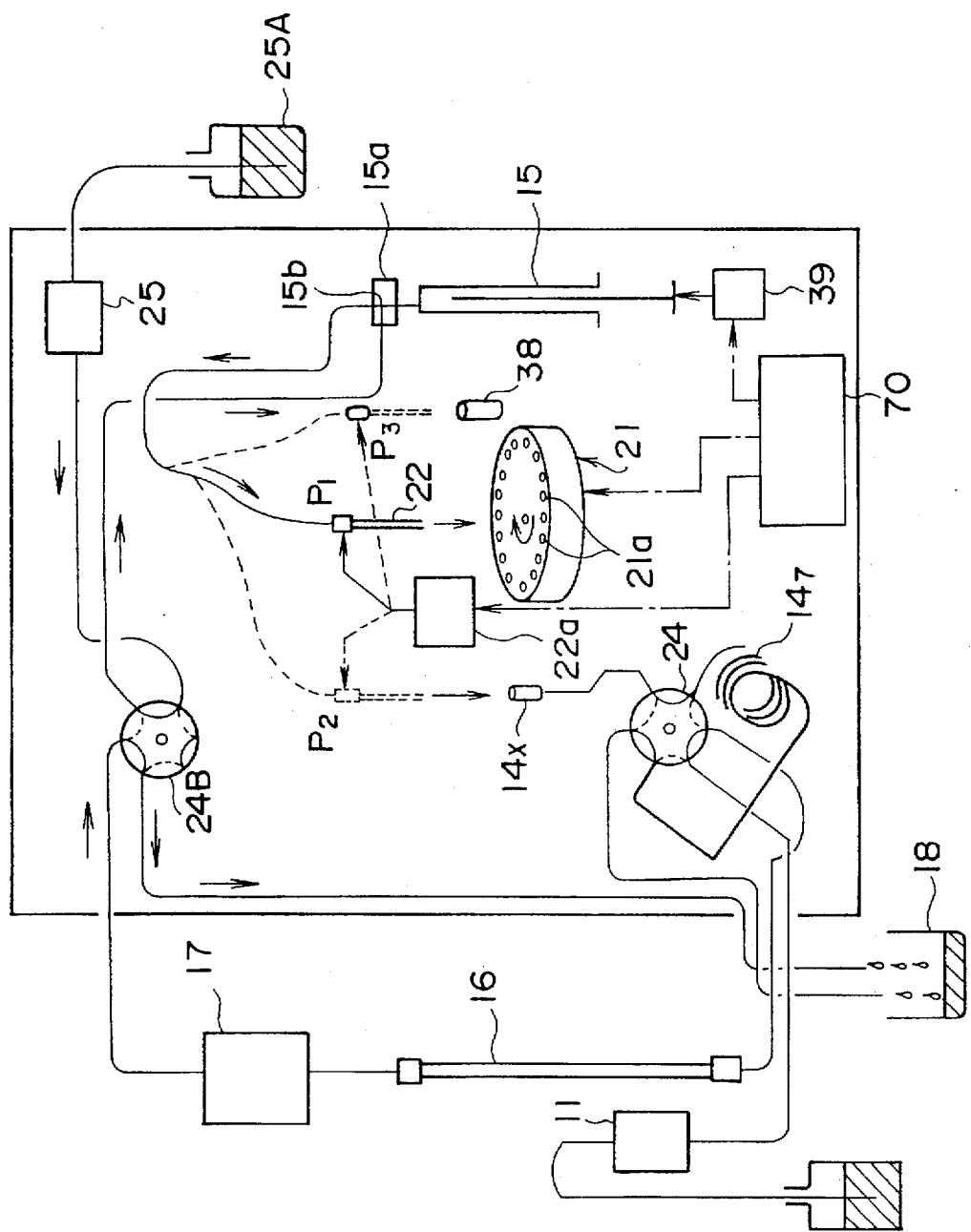
FIG. 19 is a diagram showing the construction of a liquid chromatograph according to a fifth embodiment of the present invention.
Figure 20:
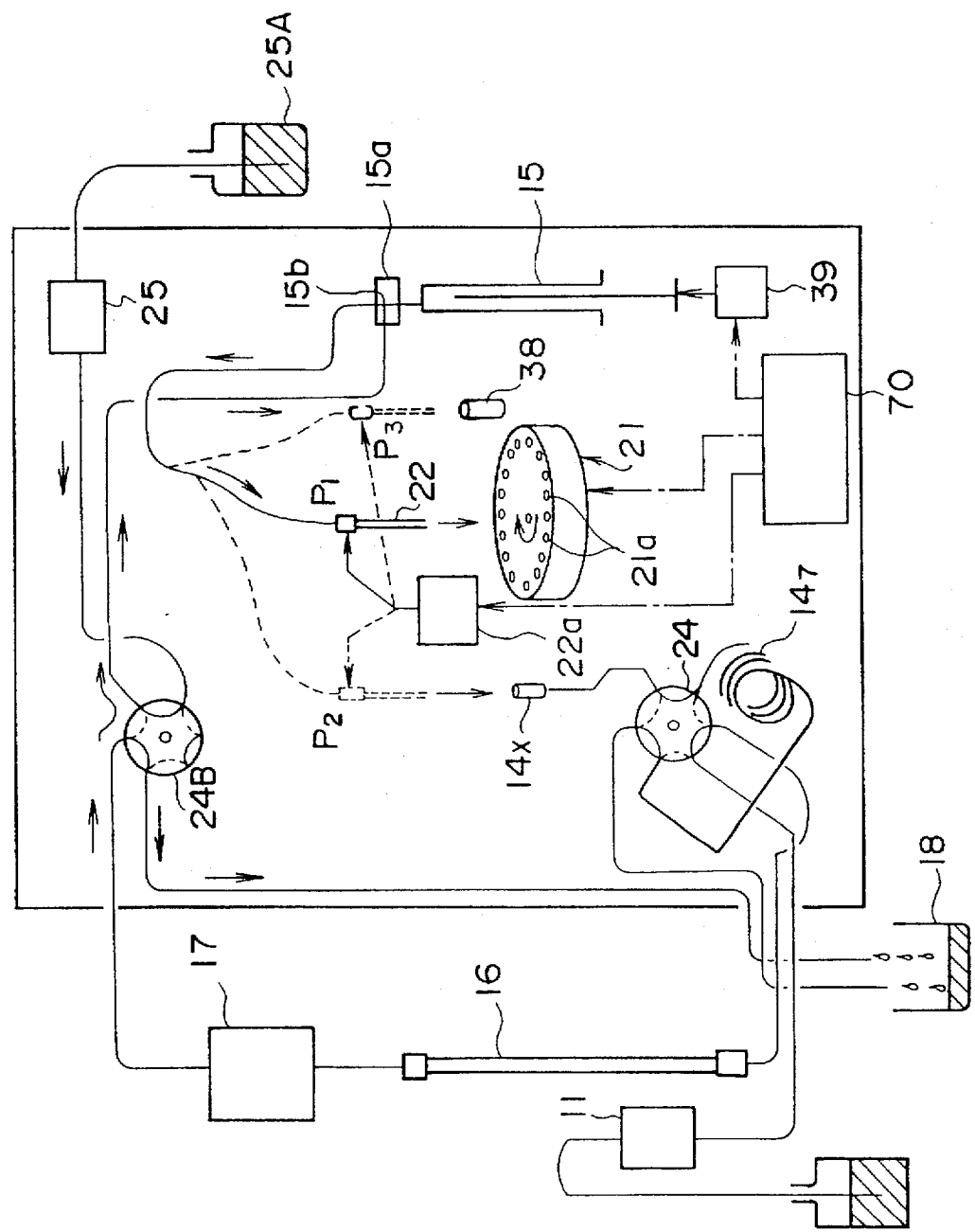
FIG. 20 is a diagram showing the liquid chromatograph of FIG. 19 in a different state.

Referring to FIGS. 19 and 20, it will be noted that the liquid chromatograph includes a system controller 70, wherein the system controller 70 controls the robot 22a and the sample holder 21 and further the syringe 15, wherein the system controller 70 controls the syringe 50 by way of an actuator 39 as well as the valve 14 and the pump 25.

Further, there is provided a vessel 38 for holding an inert liquid to be described later, separately to the sample holder 21. The vessel 38 is provided in the vicinity of the sample holder 21 such that the sample injection needle 22 can pick up the liquid held in the vessel 38 at a position $P_3$, which is different from any of the positions $P_1$ and $P_2$.

Figure 21:
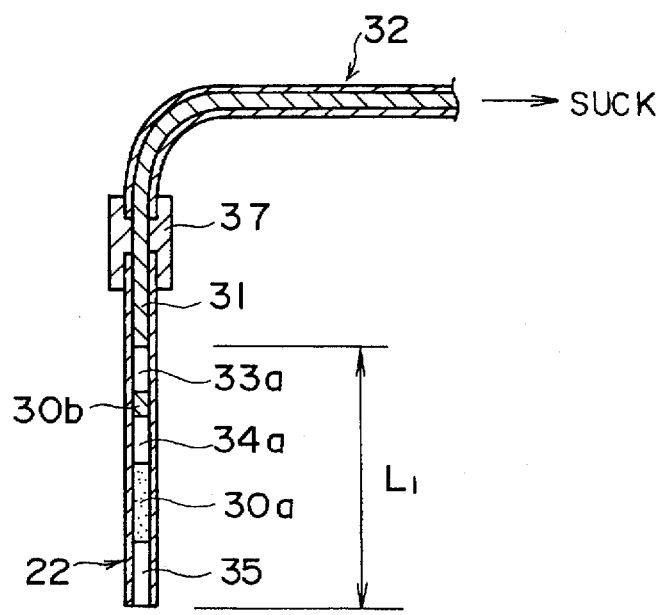
FIG. 21 is a diagram showing a pulling in of a sample solution into a sample injection tube in the liquid chromatograph of FIG. 19.
Figure 22:
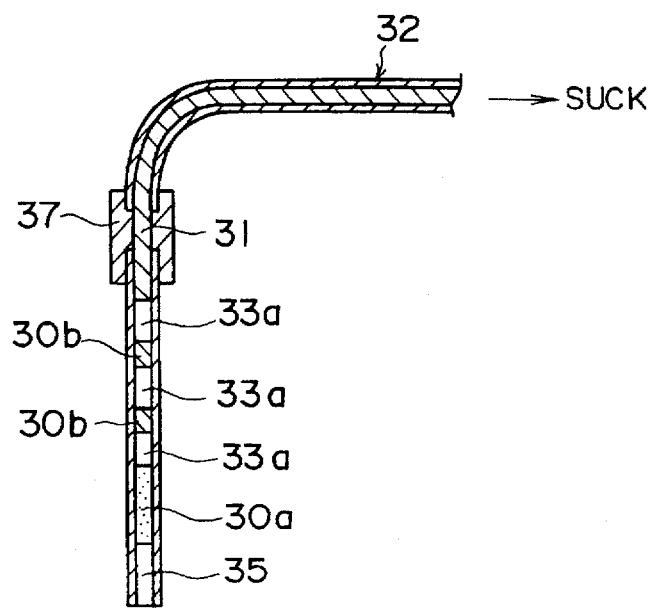
FIG. 22 is a diagram similar to FIG. 21, showing another example of pulling in a sample solution into the sample injection tube.

In the present embodiment, the system controller 70 controls the sequence of pulling of the sample into the needle 22, such that the inert liquid held in the vessel 38 is pulled first, followed by pulling in of the sample, with an intervening suction of an air gap. As a result, a droplet 30a of the sample is held in the sample injection needle 22 provided at an end of the tube 32, wherein it will be noted that the tube 32 is filled by the rinsing liquid 31 and one or more droplets 30b of the inert liquid is held in the needle 22 separated from the rinsing liquid 31 and from the sample 30a by gaps 33a as indicated in FIG. 21 or FIG. 22. When injecting the sample droplet 30a to the sample loop $14_7$, the system controller 70 energizes the actuator 39 of the syringe 15 such that the sample droplet 30a is injected first, followed by the injection of one or more of the inert liquid droplets 30b. It should be noted that the inert liquid forming the droplets 30b is formed of a substance that does not react to or modify the composition of the sample droplet 30a.

Figure 23:
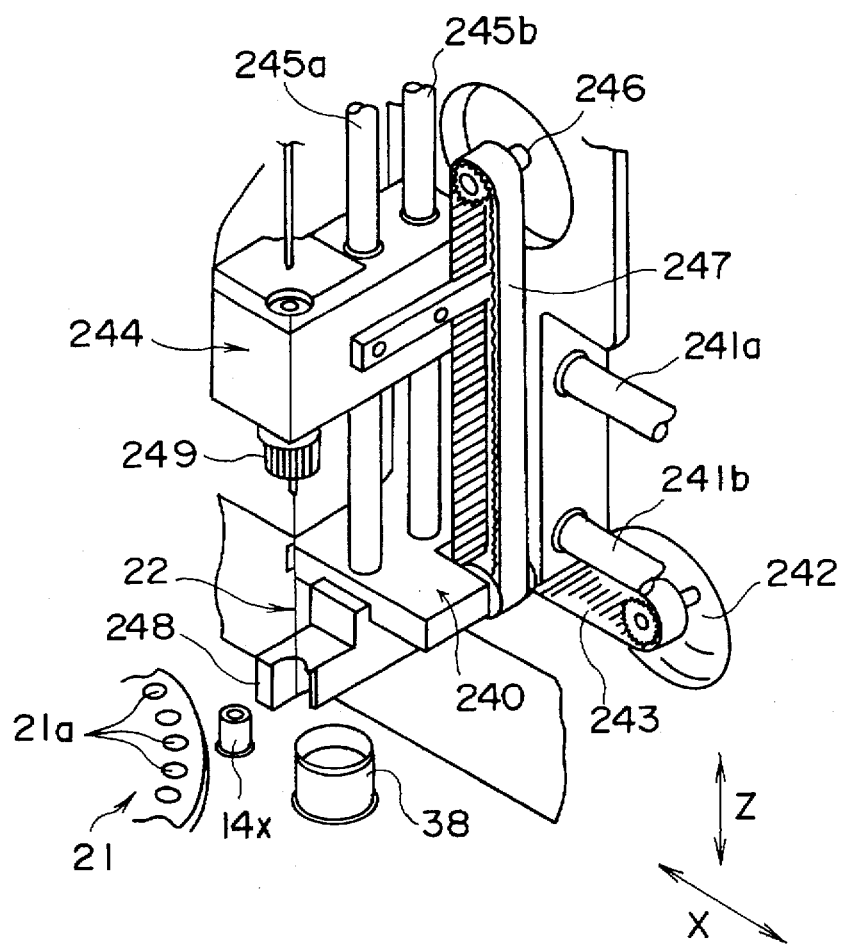
FIG. 23 is a diagram showing the construction of a mechanism used in the liquid chromatograph of FIG. 19.

FIG. 23 shows the construction of the 22a in detail.

Referring to FIG. 23, the robot 22a has a base body 240 and an arm 244 held movably with respect to the body 240. It should be noted that the base body 240 in turn is held movable on horizontal shafts 241a and 241b in the X-direction. Further, it should be noted that the arm 244 is movable along vertical shafts 245a and 245b mounted upon the body 240 in the Z-direction.

The body 240 of the robot 22a is mounted upon a chassis not illustrated, and the body 240 is moved in the X-direction with respect to the chassis by means of a stepping motor 242 and a cooperating timing belt 243. The base body 240 in turn carries a stepping motor 246, and the stepping motor 246 drives the arm 244 in the Z-direction by means of a timing belt 247.

It should be noted that the arm 244 carries the foregoing sample injection needle 22 by means of a connector 249. Further, there is provided a protective guide 248 on the base body 240 for protecting the tip end of the sample injection needle 22.

The controller 70 of FIGS. 19 and 20 energizes the stepping motors 242 and 246, and the robot 22a moves the sample injection needle 22 in the X- as well as Z-direction under control of the controller 70. As a result of such a control, the sample injection needle 22 is selectively inserted the vial 22a or into the vessel 38 that contains the inert liquid, for collecting the sample or the inert liquid into the sample injection needle 22. Further, the needle 22 is moved to the position corresponding to the injection port 14x for injecting the sample droplet 30a as well as the inert liquid droplets 30b held therein to the injection port 14x.

Next, the control achieved by the controller 70 will be described in detail with reference to the flowchart of FIG. 24.

Figure 24:
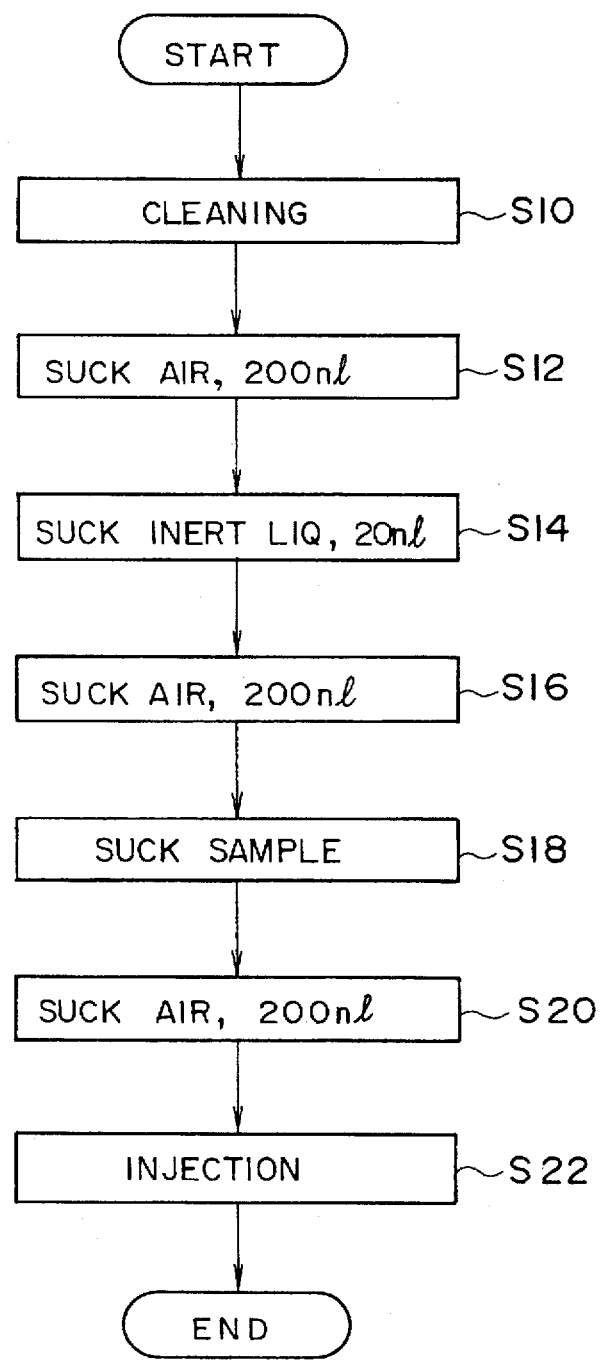
FIG. 24 is a flowchart showing the processes of pulling in the sample solution into the sample injection tube according to the fifth embodiment of the present invention.

Referring to FIG. 24, the process starts with a step S10 in which the entire piping system is cleaned by flowing a rinsing liquid therethrough.

After the step S10, the controller 70 activates the robot 22a in a step S12 such that the sample injection needle 22 is held at a position in which the tip end of the sample injection needle 22 is away from any of the sample injection port 14x, the sample vial 21a and the container 38 of the inert liquid. In this state, the controller 70 activates the syringe actuator unit 39 to cause a pulling of the air into the needle 22. Thereby, an air gap of about 200 nl is formed in the needle 22 as indicated by the numeral 33 in FIG. 21 as a result of the suction of the air.

Next, a step S14 is conducted to move the needle 22 into the inert liquid held in the vial 38 to pull the inert liquid into the needle 22. Thereby, the inert liquid droplet 30b is formed in the needle 22 with a volume typically of 200 nl. After the step S14, a step S16 is conducted to move the needle 22 away from the vial 38 to pull the air into the needle 22. As a result, another gap 33a is formed as shown in FIG. 21 with a volume typically of 200 nl. Further, the robot 22a moves, in the step S18, the needle 22 into the sample liquid held in one of the vials 21a for pulling the sample liquid into the needle 22 to form a sample droplet as shown in FIG. 21 by the numeral 30a. After the step S18, the needle 22 is moved away from the vial 21a, and the suction of the air in a step S20 is made to form another gap 35 such that the sample droplet 30a is sandwiched laterally by the gaps 34a and 35. Further, a step S22 is carried out in which the needle 22 is inserted into the sample injection port 14x and the sample droplet 30a in the needle 22 is injected to the sample loop $14_7$, followed by the injection of the inert liquid droplet 30b. In the step S22, it should be noted that the activation of the actuator 39 is controlled such that only a part of the content of the sample injection needle 22 corresponding to the part represented by $L_1$ is injected to the sample loop $14_7$. The sample liquid droplet 30a thus injected is then fed to the column 16 further to the detector 17 via the six-port valve 14 as already explained.

According to the sequence of FIG. 24 for supplying the sample to the detector 17, it should be noted that the sample droplet 30a is supplied first, followed by the inert liquid droplet 30b. In other words, any sample liquid that is left on the piping system is collected by the inert liquid droplet 30b and is supplied together with the sample droplet 30a to the column 16 and the detector 17. Thereby, the loss of the sample liquid on the inner wall of the piping system is effectively eliminated by employing the feeding sequence shown in the flowchart of FIG. 24, and a high precision analysis of the sample becomes possible. According to the experiment conducted by the inventor, it was possible to achieve a relative standard deviation (RSD) of 0.2% for the peak area when the volume of the sample is set to 2 μl. In the process of FIG. 24, it is of course possible to repeat the steps S12 and S14 to form a number of inert liquid droplets as indicated in FIG. 22.

The composition of the inert liquid depends upon the composition of the sample and the composition of the cleaning solution, wherein the composition of the rinsing liquid is determined based upon the estimated composition of the sample, and the composition of the inert liquid determined based upon the composition of the rinsing liquid. It is also possible to use a rinsing liquid as the inert liquid. The following TABLE I shows various possible combinations of the cleaning solution and the inert liquid.

TABLE I

| CLEANING SOLUTION | INERT LIQUID COMPOSITION |
| --- | --- |
| 50% methanol | 70% methanol |
| 100% methanol | 70% methanol |
| 50% acetonitrile | 50% acetonitrile |
| 50% acetonitrile | 50% acetonitrile |
| 0.01M sodium decyl sulfate (pH 2.3) | 0.01M sodium decyl sulfate (pH 2.3) |

Next, a sixth embodiment of the present invention will be described with reference to FIG. 25.

Figure 7:
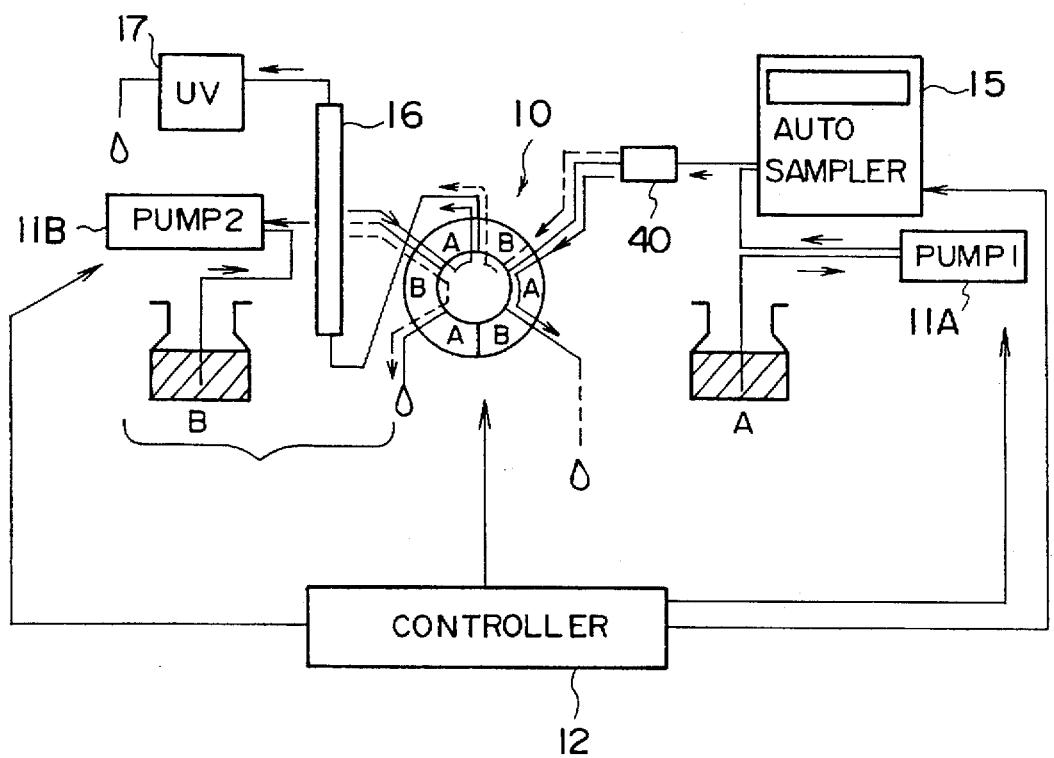
FIG. 7 is a diagram showing the construction of a conventional dual-column liquid chromatograph that uses a concentration column for prefocusing a sample solution.
Figure 25:
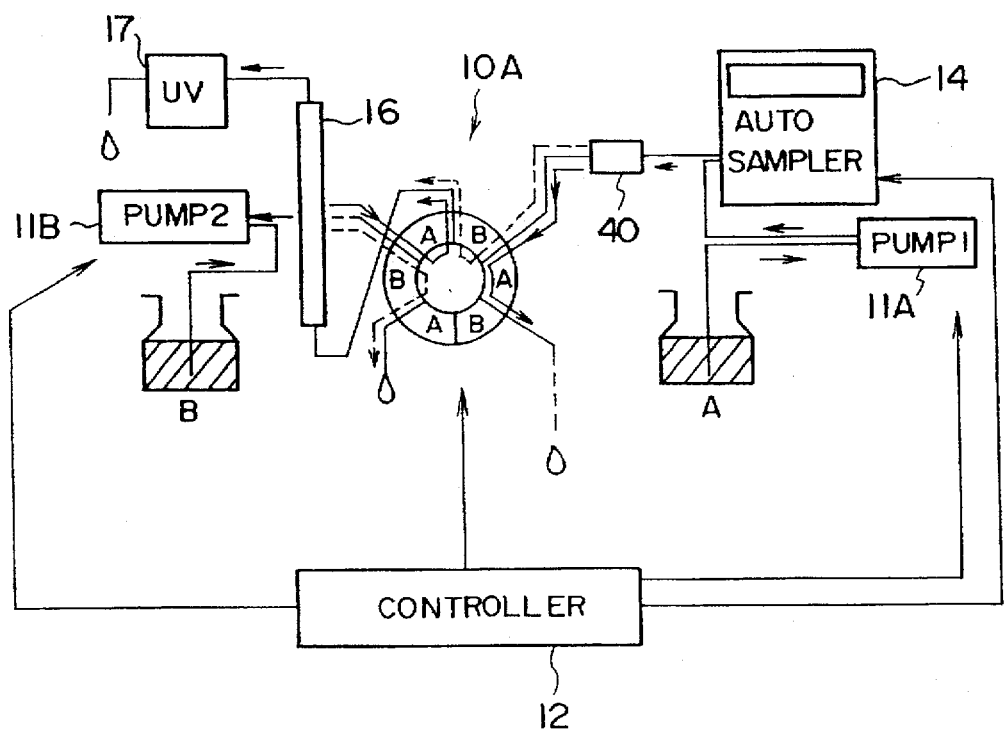
FIG. 25 is a block diagram showing the construction of a liquid chromatograph according to a sixth embodiment of the present invention.

In the embodiment of FIG. 25, it will be noted that the liquid chromatograph has a construction substantially identical with the system of FIG. 7 except that the system uses the six-port valve 24 described in FIG. 10, in place of the six-port valve 10, as a six-port valve 10A. Alternatively, one may employ the dual-valve of FIG. 17 in combination with the sample collection system described with reference to the embodiment of FIG. 13. By using the valve that is substantially free from dead volume for the valve 10A, one can achieve a substantially complete switching of the solvent. As the construction of the valve 24 and hence the valve 10A is already explained, the description will not be repeated.

In the present embodiment, the precolumn 40 uses a column packing material of a porous medium covered by a silicone polymer that has an Si—R bond and an Si—R' bond, wherein R represents a hydrophobic group while R' represents a hydrophilic group. By using such a column packing material, it is possible to separate proteins with high efficiency when a sample containing protein such as serum is analyzed. Thereby, an effective concentration of the target substance is achieved.

In the present invention, porous media commonly used in liquid chromatography such as silica gel, alumina, porous glass beads, zeolite, hydroxyapatite and graphite may be used as the packing material of the column 40. Alternatively, it is possible to use composite powders formed of a resin core covered by inorganic powders such as silica gel, titanium dioxide, hydroxyapatite, and the like. On may use materials such as polyamides, acrylic resins, polyvinyl alcohols, and the like, for the resin core.

Typically, the porous medium has a diameter of 2–200 μm and has a specific surface area of 200–300 m²/g. Further, the porous medium generally has fine pores of 40–120 Å diameter. It is particularly preferable to use a medium having a size of 3–50 μm in diameter and a specific surface area of 400–600 m²/g. The porous medium has fine pores of 60–80 Å diameter and may have a spherical shape or irregular shape.

As already noted, the porous medium is covered with a silicone compound having a Si—H group, wherein the silicone compound is generally represented by the formula

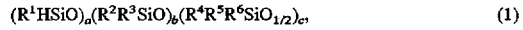  (1)

wherein each of $R^1$–$R^3$ is a hydrocarbon group having 1–10 carbon atoms, at least one of the carbon atoms may be substituted by a hydrogen or halogen atom. It should be noted that the case in which all of the groups $R^1$–$R^3$ are formed of hydrogen is excluded. Further, each of $R^4$–$R^6$ represents a hydrocarbon group containing 1–10 carbon atoms, with at least of the carbon atoms being substituted by a hydrogen or halogen atom. Further, a and b are integers equal to or larger than zero respectively, while c is equal to zero (0) or two (2). When c=0, a and b has a value in which the sum of a and b becomes an integer equal to or larger than three.

The foregoing silicone compound includes first and second group compounds below, wherein the first group compounds is a cyclic silicone compound corresponding to a case where c=0 and generally represented by the formula of

in which $R^1$–$R^3$ are defined already except that at least one of the carbon atoms may be substituted by a halogen atom and that the sum of $\underline{a}$ and $\underline{b}$ exceeds three. The representative compounds belonging to this group may be represented as

where n is an integer in the range between 3–300, or

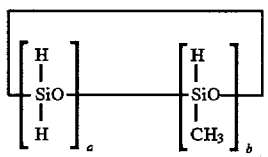

where a+b=3–300.

One may use any of the foregoing compounds individually or in the form of mixture. In any of the foregoing compounds, the value of n or a+b is preferably in the range between 3 and 7. With increasing value for the parameter n, the boiling point of the compound decreases. In other words, the compound easily evaporates and adheres upon the medium. Particularly, trimers and tetramers are preferred due to the easiness of polymerization associated with their stereochemical properties.

It should be noted that the foregoing cyclic silicone compound includes dihydrogen-hexamethylcyclotetrasiloxane, trihydrogen-pentamethylcyclotetrasiloxane, tetrahydrogen-tetramethylcyclotetrasiloxane, dihydrogen-octamethylcyclopentasiloxane, trihydrogen-heptamethylcyclopentasiloxane, tetrahydrogen-hexamethylcyclopentansiloxane, and pentahydrogen-pentamethylcyclopentasiloxane.

On the other hand, the second group silicone compound described before corresponds to the case where c=2 in the foregoing formula (1) and that $R^1$–$T^6$ are hydrocarbon group in which at least one of carbon atoms is substituted by a halogen atom. A typical silicone compound of this group is represented as

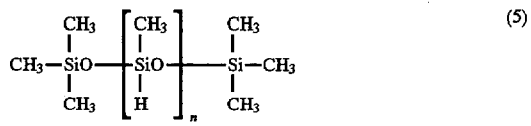

where n represents an integer between 2–100.

The foregoing compound of formula (5) includes 1,1,1,2,3,4,4,4-octamethylsiloxane, 1,1,1,1,2,3,4,5,5,5-nonamethylpentasiloxane, and 1,1,1,2,3,4,5,6,6,6decamethylhexasiloxane.

The silicone compound having the general formula (1) is contacted to the forgoing porous medium either in the vapor phase state or liquid phase state. When contacting the silicone compound in the form of vapor phase, a hermetically sealed vessel is used, in which molecules of the foregoing silicone compound vapor are contacted with the surface of the porous medium at a temperature of less than 120° C., preferably less than 100° C., under a pressure of less than 200 mmHg, preferably less than 100 mmHg. Alternatively, a mixed gas of the foregoing silicone compound and a carrier gas may be used for contacting with the porous medium of the filler. This vapor phase process is preferably conducted for those silicone compounds such as tetrahydrotetraethylcyclotetrasiloxane, tetrahydrotetramethylcyclotetrasiloxane, and the like.

In the liquid phase process, on the other hand, a volatile solvent that dissolves the foregoing silicone compound such as benzene, chloroform or particularly hexane is used, and a solution of the silicone compound of 0.01–1 weight percent is prepared. The solution thus prepared is added to the porous medium with such a proportion that 0.01–1 parts by weight of the silicone compound is added to 1 part by weight of the medium while stirring the solution thus obtained. Thereafter, the mixture of the silicone compound and the porous medium is held at a temperature of 50°–200° C. for more than two hours to cause a polymerization on the surface of the medium.

It should be noted that the foregoing surface polymerization is promoted by the active points on the surface of the medium and no particular catalyst is necessary. Here, the "active point" means a part that promotes the polymerization of the silicone compounds that includes a siloxane (Si—O—Si) bond or a hydrosylile (Si—H) bond, and includes various acid points, basic points, oxidizing points and reduction points. The surface polymerization proceeds until the active points on the medium are all covered by a film of silicone polymer. When the activity of the medium is very low, one may treat the medium, before or after the contacting process, by an alkaline catalyst such as sodium hydroxide, lithium hydroxide, ammonium hydroxide, and the like, or by an alkyl metal catalyst such as dibuthyltin.

Two different structures are known for the silicone polymer that covers the surface of the filler medium. The one being a silicone polymer in which polymerization occurs as a result of disconnection and recombination of the siloxane bond (—Si—O—Si—), and the polymer includes only the —Si—O—Si— chain. The other being a silicone polymer in which the polymerization occurs as a result of bridging of hydrosylile (Si—H) bonds under presence of $H_2O$ or $O_2$. In this case, the polymerization proceeds as

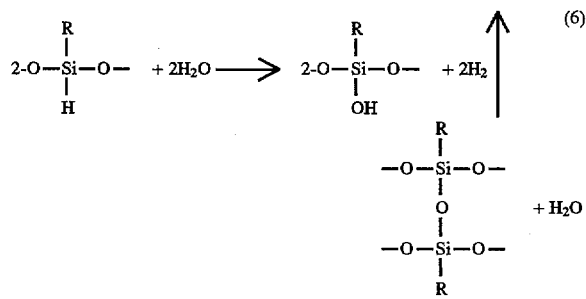

and the silicone polymer includes a network structure of

therein.

The foregoing two types of polymerization may occur independently or proceed simultaneously, depending upon the medium or the polymerization condition such as the temperature and catalyst. Further, the degree of polymerization may change variously.

It should be noted that, in the process described heretofore, the silicone compound having a small molecular weight penetrates inside the minute pores on the filler medium, such that substantially entire surface of the filler medium, including the pore inner surface, is covered by the silicone compound that forms a film having a thickness of 3–30 Å. In this process, it should be noted that the porous structure of the medium is preserved. Further, the porous structure of the medium is preserved after the deposition of vinyl compound that follows the deposition of the silicone polymer compound.

The silicone polymer compound thus formed on the surface of the porous medium generally have a molecular weight (weight average molecular weight) of 150,000 or more. It is known that silicone compounds becomes less soluble to water or organic solvents with the progressing degree of polymerization. Thus, it is generally not possible to extract the polymer for measurement of the molecular weight. It is also not possible to measure the molecular weight of the polymer in the state that the polymer forms a coat on the surface of the medium.

In order to measure the molecular weight under such a situation, the polymers are extracted in various stages of the polymerization reaction by using chloroform. In this procedure, it was confirmed that there exists a polymer of which molecular weight reaches 150,000 in the maximum. This in turn indicates that the polymer should have a molecular weight exceeding 150,000 before it is extracted by chloroform. On the other hand, further analysis of the molecular weight is difficult.

hydrophobic groups

Meanwhile, the silicone polymer covering the surface of the filler medium includes unreacted Si—H groups. Thus, by reacting hydrocarbon that contains vinyl in the molecule, upon the Si—H group, it is possible to form a silicone polymer that contains the Si—C bond. For this purpose, one may use a vinyl compound having a general formula of $$R_8-CH=CH-R_9 \tag{8}$$

in which each of $R_8$ and $R_9$ may be an alkyl group containing 1–40 carbon or hydrogen atoms, a cycloalkenyl group containing 4–8 carbon atoms, and an alkenyl group that may be substituted by alkyl containing 1–20 carbon atoms.

The foregoing vinyl compound includes ethylene in which both of $R_8$ and $R_9$ are hydrogen, a vinyl compound such as α-olefin compound in which one of the $R_8$ and $R_9$ is hydrogen and the other is a group other than hydrogen, a symmetric vinyl compound in which both of $R_8$ and $R_9$ are a group other than hydrogen, and an asymmetric vinyl compound in which $R_8$ and $R_9$ are different groups other than hydrogen. Preferably, the vinyl compound includes a compound in which each of $R_8$ and $R_9$ is an alkyl group containing 4–20 carbon atoms such as a 1-hexyl group, 1-octyl group, 1-decyl group, 1-dodecyl group, 1-hexadecyl group, 1-octadecyl group, cyclohexyl group or a cyclohexenyl group; phenyl or naphtyl group; or phenyl or naphtyl group substituted by a lower alkyl group containing 1–4 carbon atoms.

When a compound that contains hydrogen for the group $R_8$ and the group $R_9$ formed either of ethyl group, hexadecyl group and the phenyl group, is used for the vinyl compound, conventional chemical bond type packing materials known as $C_4$-type, $C_8$-type, $C_{16}$-type and the phenyl type are obtained. The reaction between the foregoing vinyl compound and the silicone polymer power may be achieved for example at a temperature of 50°–300° C. under presence of a solvent for two or more hours. In such a reaction, catalyzers such as Ru, Rh, Pd, Os, Ir, Pt, and the like may be used.

The foregoing reaction of the vinyl compound and the silicone compound is confirmed by means of diffusion reflection spectroscopy conducted by an FT-IR analyzer. It should be noted that, as a result of the reaction to add the vinyl compound, the absorption of the Si—H group at 2160 $cm^{-1}$ decreases substantially, and a new absorption peak of alkyl group appears at a wavelength of 2800 $cm^{-1}$–3000 $cm^{-1}$. By obtaining the ratio of the absorption peaks, it is possible to estimate the degree of the reaction.

hydrophilic groups

In order to form the packing material of the liquid chromatography of the present embodiment, it is further necessary to modify a part of the SiH groups of the silicone polymer coating covering the surface of the packing material, to be hydrophilic. For this purpose, one may use tetraol according to the reaction below.

(9)

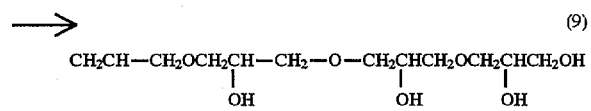

The synthesis of tetraol is achieved as follows.

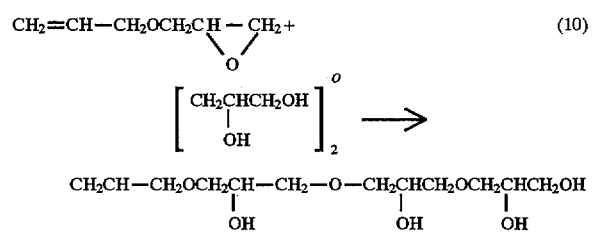

(10)

Further, it should be noted that polyol is formed by replacing diglycerin by polyglycerin, and polyol thus formed can also be used as the hydrophilic group of the present invention. Furthermore, it is possible to use polyoxyethylenarylether shown in the formula (10), wherein polyoxyethylenarylether is synthesized by adding ethylene oxide to oxide to allylalchol.

The packing material thus obtained has a distinct advantage over conventional packing material of chemical bonding type in that the packing material is effective in a wide range of pH of 2–10. Particularly, it should be noted that the packing material can be used in alkali solvents and that the packing material provides an improved safety. It should be noted that conventional fillers could not be used in alkali solvents.

The present invention eliminates the necessity of complicated sample preparation and is particularly advantageous in the liquid chromatographic analysis of various drugs or metabolic products in a biological body such as serum. It is possible to directly inject biological samples for analysis and obtain a high precision analysis. It should be noted that the packing material of the present invention is of complete polymer coated type and does not use Lewis acid. Thus, it is possible to extract basic materials such as 2-ethylpyridine or N,N'-dimethylaniline.

hydrophobic-to-hydrophilic modification process

Figure 27A:
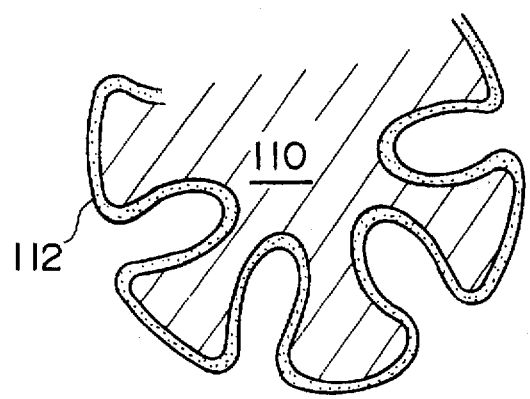
FIGS. 27A–27C are diagrams showing the process of forming hydrophilic and hydrophobic sites on a silicone polymer film that covers the surface of a filler that is used in the liquid chromatograph of the sixth embodiment.
Figure 27B:
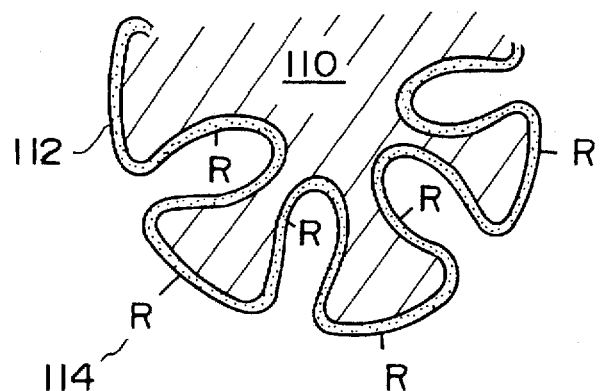

The packing material of the present embodiment is formed by modifying the surface of a silicone polymer covering a porous medium to be hydrophobic, followed by a process for modifying the surface to be hydrophilic. Thus, a silicone polymer is used first to form a coating 112 on the surface of a porous medium 110 as indicated in FIG. 27A. Thereby, only a part of the —SiH groups of silicone are used for polymerization, while the rest of the —SiH groups remain unused. Thus, in a step of FIG. 27B, the remaining —SiH groups and a hydrophobic groups (R) 114, which contain a double bond therein, are reacted as indicated in FIG. 27B to form a —SiR group. In the step of FIG. 27B, the amount of the hydrophobic group R and/or the reaction condition are controlled such that not the entire —SiH groups are consumed. Thus, there still remain unreacted —SiH groups on the surface of the silicone film 112.

Figure 27C:
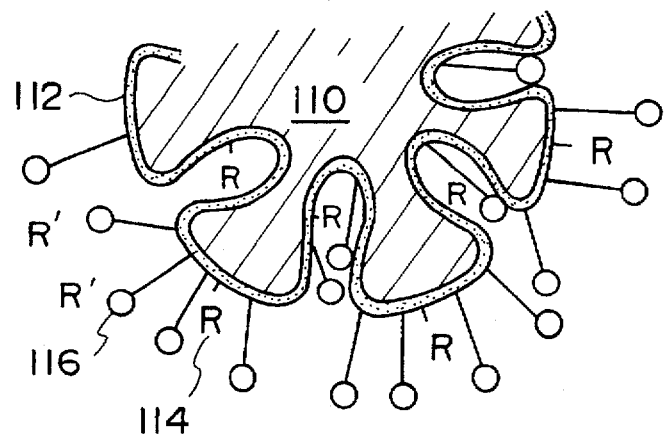

Next, in a step of FIG. 27C, the remaining —SiH groups on the silicon polymer coating 112 are reacted with a hydrophilic groups (R') 116 that contain a double bond therein, to form hydrophilic groups SIR'. In the state of FIG. 27C, it should be noted that the surface of the silicone polymer 12 shows a mixed function structure of the hydrophobic groups and simultaneously the hydrophilic groups. By changing the proportion of the hydrophobic and hydrophilic groups 114 and 116, it is possible to obtain a peculiar extraction characteristics. The hydrophobic-hydrophillic modification process is advantageous in view point of easy control of the introduction of the hydrophobic groups. It should be noted that the hydrophilic modification provides a particularly significant influence upon the holding characteristics of the packing material.

hydrophilic-to-hydrophobic modification process

Figure 28A:
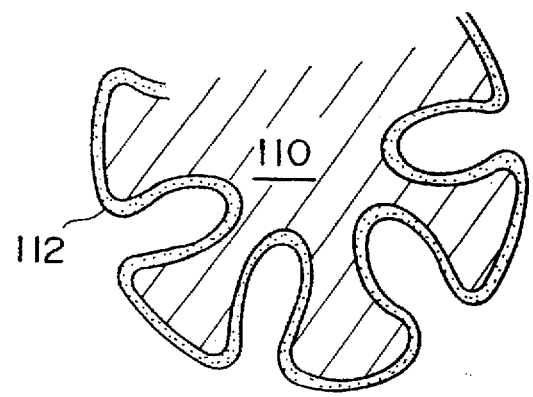
FIGS. 28A–28C are diagrams showing another process of forming hydrophilic and hydrophobic sites on a silicone polymer film that covers the surface of a filler used in the liquid chromatograph of the sixth embodiment.
Figure 28B:
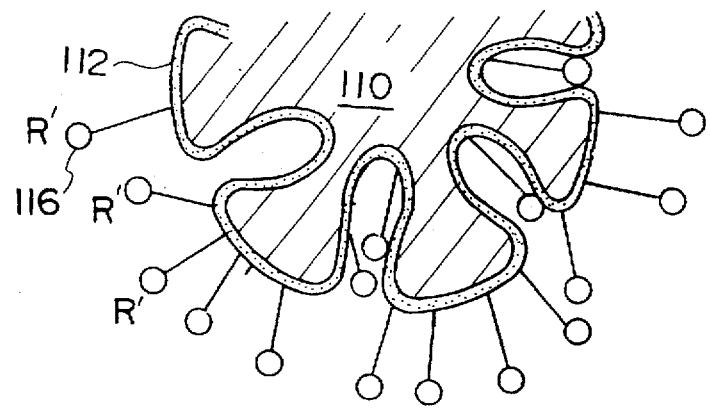

In the packing material according to the present embodiment, the surface of a porous medium 110 is covered by a silicone polymer film 112 first as indicated in FIG. 28A, followed by a process for modifying the surface to become hydrophilic as indicated in FIG. 28B. In the process of FIG. 28B, it should be noted that the —SiH groups remaining on the surface of the silicone polymer 12 are reacted with the hydrophilic groups (R') 116 that includes therein a double bond to form —SIR' groups. In the process of FIG. 28B, it should be noted that the amount of the hydrophilic groups R' or the conduction of the reaction is adjusted such that not all of the —SiH groups on the polymer film 112 are consumed.

Figure 28C:
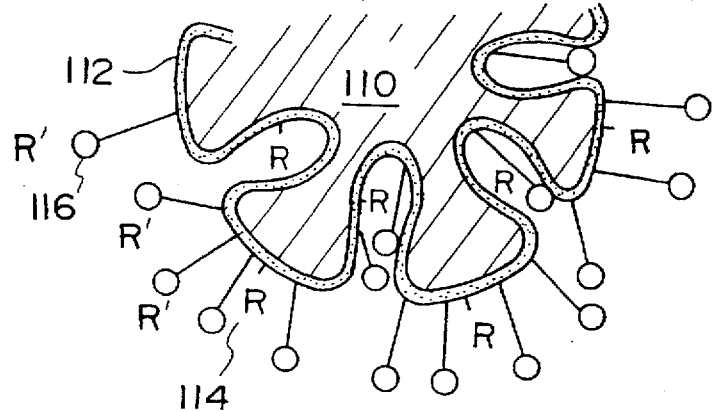

The surface thus treated is further subjected to a process of FIG. 28C, in which hydrophobic groups (R) 114 that includes therein a double bond, are introduced to react with the remaining —SiH groups on the surface of the silicone polymer film 112.

In the process of the present embodiment in which the modification of the polymer surface to be hydrophilic is conducted first, it is possible to modify a large part of the surface to be hydrophilic. As a result, the adsorption of protein molecules upon the polymer surface is minimized. The process of modifying the surface to be hydrophilic is preferably conducted in water. It should be noted that silica gels covered by silicone polymer generally show a repellency, and the reaction starts from the surface outside the pores. Thus, it is thought that the exterior of the pores are more hydrophilic as compared with the interior of the pores. This in turn indicates that the process of becoming hydrophobic occurs more in the interior of the pores as compared with the exterior of the pores.

simultaneous process of hydrophobic and hydrophilic modification

The porous packing material covered with silicon polymer of the present embodiment may be formed by conducting the process of modifying the medium surface to be hydrophobic and the process of modifying the medium surface to be hydrophilic simultaneously.

Thus, in the step of FIG. 29A, the porous medium 110 is covered by a silicon polymer to form the polymer film 112. Next, in the step of FIG. 29B, the —SiH group on the surface of the silicone polymer film 112 are reacted with hydrophobic groups (R) 114 and simultaneously with hydrophilic groups (R') 116 each having a double bond at an end thereof.

The process of the present embodiment is advantageous in that the reaction is made only once. By reducing the proportion of the compounds acting as a source of the hydrophobic groups such as styrene with respect to the compounds that act as a source of the hydrophilic groups such as tetraol, polyol, and the like, it is possible to obtain the desired packing material due to the difference in the reactivity. It is thought that the hydrophobic compounds have smaller volume than hydrophilic compounds and have a higher reactivity. In the process of the present embodiment, it is possible to use alcohol as a solvent. Thereby, it is also possible to mix styrene and tetraol simultaneously.

hydrophobic modification-expoxidation-hydrophitic modification process

In the present embodiment, the packing material is prepared by covering the surface of a porous packing material 110 by a silicone polymer film 112 as shown in FIG. 30A, followed by a process of modifying the surface of the polymer film 112 to become hydrophobic as indicated in FIG. 30B. In the process of FIG. 30B, hydrophobic groups (R) 114 that includes a double bond therein are reacted with the —SiH groups on the film 112. Similarly as other embodiments described heretofore, the reaction for introducing the hydrophobic groups is controlled, by way of control of the amount of the hydrophobic groups or the reaction condition, such that not all of the hydrophobic groups on the surface of the polymer film 112 are used.

Further, a process is conducted in a step of FIG. 30C to introduce an epoxy compound that contains epoxy group 18 therein. The epoxy group 18 thus introduced have a double bond therein and are bonded with the unreacted —SiH groups on the silicon polymer film 112 by way of the double bond. Further, hydrophilic groups 120 are introduced as indicated in FIG. 30D, wherein the hydrophilic groups 120 bond against the free end of the epoxy groups 118 previously introduced in the step of FIG. 30C. As a result, there are formed hydrophilic groups (SIR') 116 from the epoxy groups 118 and also from the hydrophilic groups 120.

By employing the process of FIGS. 30A–30D, it is possible to increase the density of hydrophilic sites of the silicon polymer further. In the present process, it should be noted that a group having a smaller volume than tetraol such as acrylglycidyl ether is introduced after the step of introducing the hydrophobic groups, followed by a reaction of glycerin or diglycerin, wherein acrylglycidyl ether has a double bond at an end and an epoxy group at the other end. As a result of the increased density of hydrophilic sites, the packing material of the present embodiment provides an increased yield of recovery of proteins. In a more specific example, a hydrophobic group such as a phenyl group is introduced first, followed by a bonding of acrylglycidyl ether that has a double bond at an end and an epoxy group at the other end. Further, a group such as diglycerin or glycerin that has a hydrophilic group, —OH or —COOH being an example, is bonded upon the epoxy group.

The reaction (hydrosilylation) between the hydrophobic group or the group having a double bond at an end such as acrylglycilether, is achieved under existence of Pt catalyst. Further, the reaction between the epoxy group and compounds such as diglycerine is conducted under presence of Lewis acid, quaternary ammonium salt, tertiary amine, and the like. Alternatively, it is possible to merely open the epoxy ring in a acid solution after addition of acrylglycidyl ether to form diol.

Figure 26:
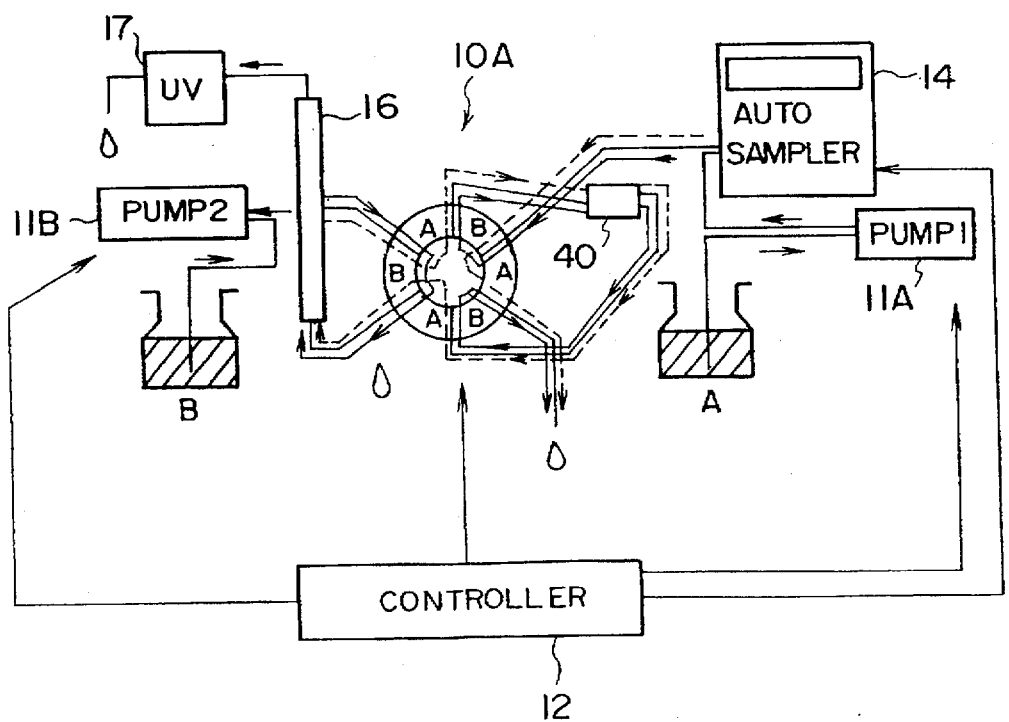
FIG. 26 is a block diagram showing the liquid chromatograph of FIG. 25 in a different state.
Figure 31A:
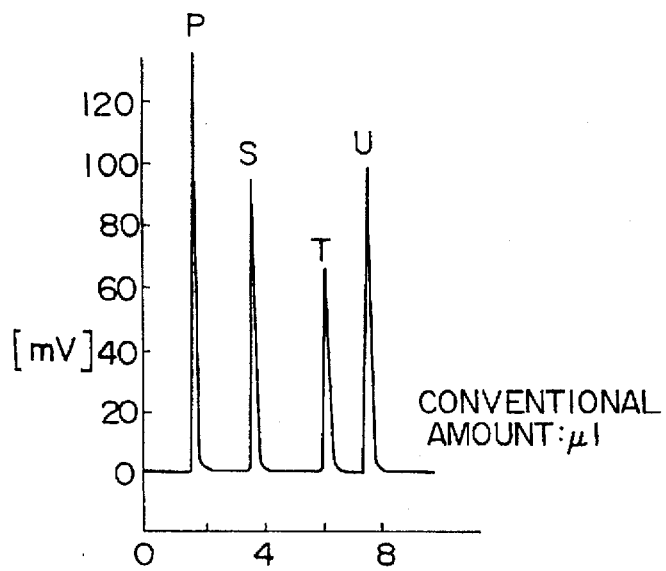
FIGS. 31A–31C are diagrams showing the effect of concentration achieved in the sixth embodiment of the present invention.
Figure 31B:
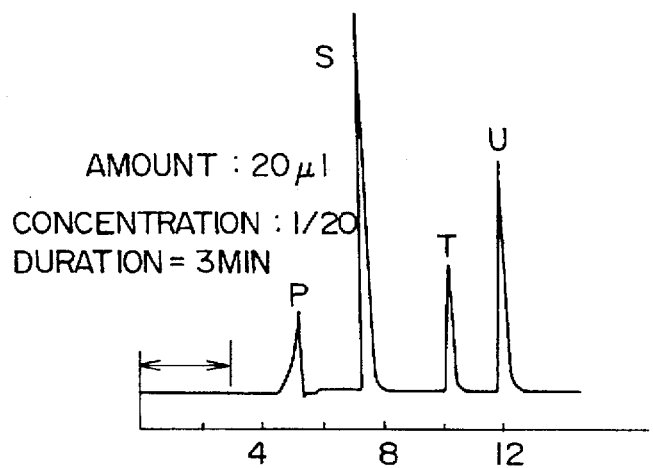
Figure 31C:
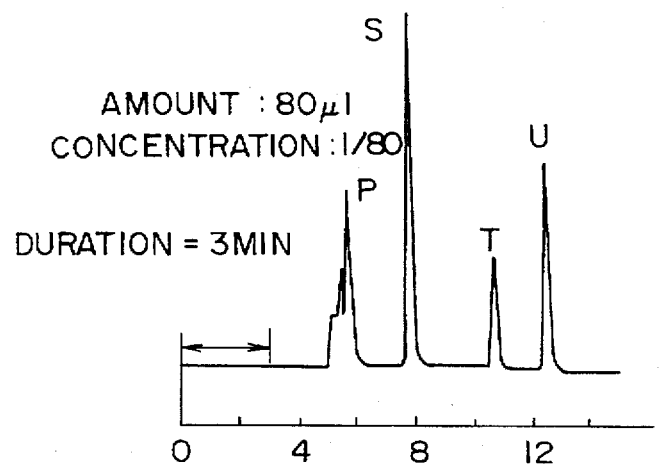

FIGS. 31A–31C show the result of liquid chromatography obtained by the instrumentation of FIG. 26, which is a modification of the construction of FIG. 26 and designed for analyzing dilute samples.

Referring to FIG. 26, the sample solution containing the target substance is supplied, in a first state of the six-port valve 10A, from the autosampler 14 and is caused to flow through the precolumn 40 as indicated by a continuous line in FIG. 26. Thereby, the target substance is captured by the packing material of the precolumn 40 and held therein with an increased concentration level. In this state, the solvent B is supplied to the separation column 16 from the pump 11B without the target substance being incorporated therein. Next, the valve 10A is switched to a second state wherein the solvent B is pumped into the precolumn 40 through the valve 10A. Thereby, the target substance held in the precolumn 40 is eluted, together with the solvent B, to the separation column 16 along a path indicated by a broken line.

It should be noted that FIG. 31A shows a case in which a conventional column packing material is used for the precolumn 40. On the other hand, FIGS. 31B and 31C show the result in which the packing material of the present embodiment is used. In the experiments of FIGS. 31B, it should be noted that a sample diluted to a concentration level of 1/20 was introduced with an amount of 20 µl, and the concentration was made in the precolumn 40 with a duration of 3 minutes. In the case of FIG. 31C, on the other hand, a sample diluted to a concentration level of 1/80 was introduced with an amount of 80 µl, wherein the process of concentration was carried out for 3 minutes.

As can be seen clearly from FIGS. 31B and 31C, the peak S of the target substance to be analyzed appears with the same sharpness as compared with the conventional case of FIG. 31A, while the peak P indicative of the components not to be retained such as proteins, are suppressed substantially. Obviously, this intensity of the sample peak S and the decreased intensity of the protein peak P indicate that the proteins are not adsorbed on the hydrophilic outer surface of the packing material in the precolumn 40. As the column packing material of the present invention does not use enzymes, it is possible to achieve a improved stability, which in turn leads to an improved reproducibility of analysis.

Figure 32:
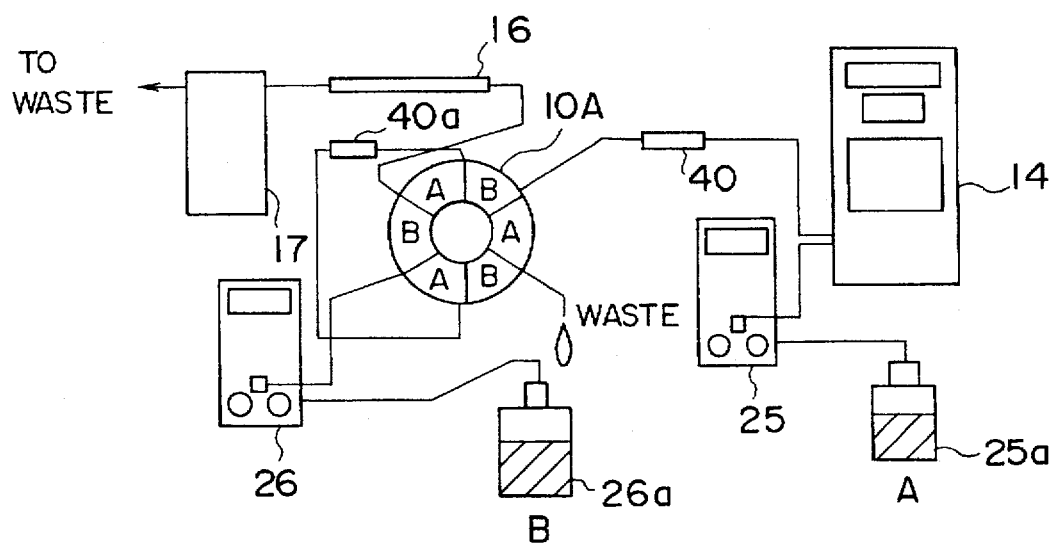
FIG. 32 is a diagram showing the construction of a liquid chromatograph according to a seventh embodiment of the present invention.

Next, a seventh embodiment of the present invention will be described with reference to FIG. 32. In FIG. 32, those parts constructed identically with the parts described already are designated by the same reference numerals, and the description thereof will be omitted.

In the present embodiment, it should be noted that there is provided a second concentration column $14_9$ between the injection port $14x$ and the six-port valve 14, for concentrating the sample in a sample solution. The sample solution is a mixture of the sample and a first solvent to be described. The column $14_9$ typically has an inner diameter of 1–4 mm and has a relatively small length of about 10–50 mm. The column $14_9$ thereby has a volumetric capacity of about 200 µl, and filled with a packing material that achieves the separation of the sample.

It should be noted that the use of the column $14_9$ having a small length is, although not capable of providing a necessary logical number of plates for achieving quantitative analysis, advantageous in view point of relaxing the pressure increase, particularly in the case where biological samples that tend to contain impurities are repeatedly injected. In the column 40, the velocity of the solvent or mobile phase is set to be 0.1–1.0 l/min.

The sample solution that has passed through the column 40 is then supplied to the next column 40a described previously for a second concentration process, wherein the column 40a may have an inner diameter of 2.0 mm and a length of 35 mm.

It should be noted that the column 40 is located in the upstream side of the column 40a. Thus, it will be noted that the embodiment of FIG. 32 is constructed such that the upstream side column 40 has a larger inner diameter as compared with the downstream side column $14_8$. Thus, the sample injected by the autosampler 14 travels consecutively through the columns 40 and 40a, and each time experiences a concentration. After concentration in the columns 40 and 40a, the sample is supplied to the separation column 16 for extraction, wherein the column 16 may typically be a micro-column and has an inner diameter of 1.0 mm and a length of 250 mm. The construction of using a plurality of concentration columns, at least one of which has a larger diameter than that of the main separation column, is particularly advantageous for micro-liquid chromatography that uses a micro-column or semi-micro column for the column 16.

Figure 33A:
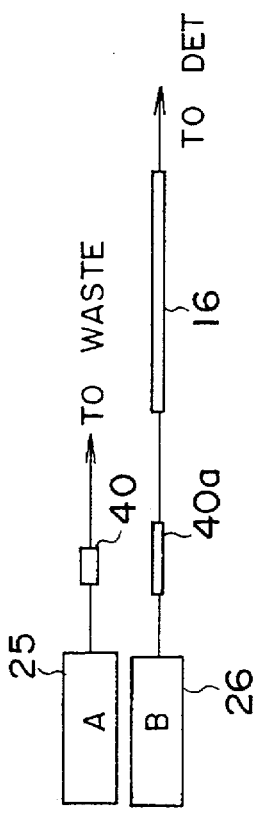
FIGS. 33A and 33B are diagrams showing the liquid chromatograph of FIG. 32 in two different states.

In operation, the valve 10A is set to a state shown in FIG. 33A and the sample is injected by the autosampler 14 into the precolumn 40. Thereby, the pump 25 is driven such that a flow rate of 0.5–1.0 ml/min is obtained for the solvent A, and proteins or other unwanted components are caused to pass through the precolumn 40 without being captured therein. In the state of FIG. 33A, the solvent B is supplied to the column 40a and further to the column 16, but without the target substance to be analyzed.

Figure 33B:
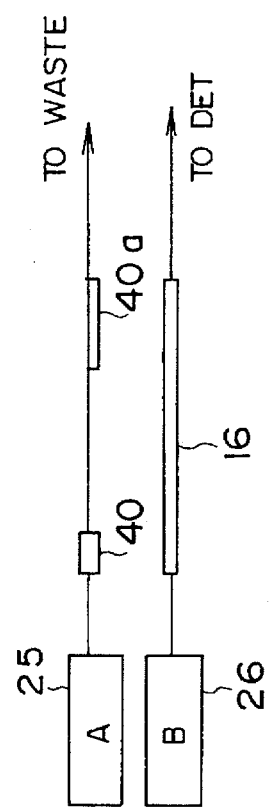

When the target substance starts eluting from the precolumn 40 in the state of FIG. 33A, the six-port valve 10A is switched to a state of FIG. 33B, wherein the sample concentrated in the precolumn 40 is now eluted and forwarded to the column 40a by the solvent A. Again, unwanted components pass through the column 40a and a concentration of the target substance occurs in the column 40a. In the state of FIG. 33B, the solvent B flows through the separation column 16 without being concentrated therein.

Further, the valve 10A is switched again to the state of FIG. 33A, wherein the substance concentrated in the column 40a starts migrating through the column 16.

In the switching operation of the valve 10A from the state of FIG. 33A to FIG. 33B, it has been necessary to change the flow rate of the pump 25 in order to avoid excessive pressure increase in the column 40a. In the present embodiment, which uses a column having an inner diameter of 1.0–4.0 mm and a length of less than 50 mm for the column 40a, it is possible to maintain the flow rate at a relatively high level, in the order of 0.1–0.5 ml/min. Thereby, unwanted increase of the duration of analysis, caused by such a reduced flow rate of the pump 25, is successfully eliminated, and one can conduct the desired analysis with a reduced operational time of the chromatograph.

In the system of FIGS. 33A and 33B, the flow rate is set to a level corresponding to the micro- or semi-micro-columns. A typical example of such a flow rate is listed in the following TABLE II as a function of the column diameter of the separation column 16.

TABLE II

| column diameter (mm) | flow rate (ml/min) |
| --- | --- |
| 2.0 | 0.2 |
| 1.5 | 0.1 |
| 1.0 | 0.5 |
| 0.8 | 0.3 |
| 0.3 | 0.05 |

By employing the system of FIG. 32, it is possible to conduct a chromatography of a large volume sample by means of micro- or semi-micro column without excessive time for analysis, by concentrating the sample by means of the columns 40 and 40a. According to the construction of the present embodiment described with reference to FIGS. 32 and 33, the time needed for measurement is reduced significantly. It will be noted that one minute injection of the sample into the concentration column 40 with the solvent flow rate of 0.5 ml/min causes a supply of 0.5 ml sample solution to the concentration column 40. When the concentration column 40a has an inner diameter of 2.0 mm and the length of 35 mm, the supply of 0.5 ml sample solution, with the designed solvent flow rate of 0.25 ml/min, results in a completion of sample concentration in about 2 minutes. As the dead volume of the column 40a is in the order of 0.06 ml, the supply of the sample solution further to the column 16 is completed in about 1 minute when a column having an inner diameter of 1 mm is used for the column 16.

The foregoing result is a significant improvement over the two column system of FIG. 25 in which much longer time is needed for separating the sample solution in the column 16. When a column having an inner diameter of 1 mm is used for the column 16 in combination with the column 40 having an inner diameter of 2.0 mm and a length of 35 mm, under the same solvent flow rate condition of 0.5 ml/min, it has been needed to have about 10 minutes to complete the separation of the sample in the column 16 due to the sudden decrease of the flow rate in the column 16. When a column having an inner diameter of 0.8 mm is used, on the other hand, much longer time, as long as 25 minutes is needed. In other words, a reduction of time of as much as 20 minutes is possible by employing the construction of the present embodiment as compared with the conventional two column system.

Further, it should be noted that the volume of the sample solution flowing into the column 16 becomes minimum in correspondence to the dead volume of the column 40. Thereby, the operation of the separation column 16 for separating the sample is stabilized substantially.

In the present embodiment that uses three columns and two solvents, with two pumps 25 and 26 for pumping the respective solvents, it is possible to supply the solvent 25a by way of the pump 25 to the column while the concentration of the sample in the concentration column 40 is simultaneously in progress. Thus, it is possible to quickly stabilize the state of the separation column 16 when the six-port valve is switched upon completion of the concentration process in the column 40. Thereby, the problem of rugged detection peak in the output waveform of the detector 17 is eliminated, and a substantial improvement is achieved about the reproducibility as well as reliability of the analysis.

Further, it should be noted that the liquid chromatograph of the present embodiment eliminates the direct communication between the column 40 and the column 16. Thus, the column 40 by no means experiences a high pressure exceeding 10 MPa in any moment of the liquid chromatographic analysis. It should be noted that increased pressure in the concentration column invites a decreased precision of the analysis. In the present embodiment, such a degradation of the analysis does not occur.

Figure 34:
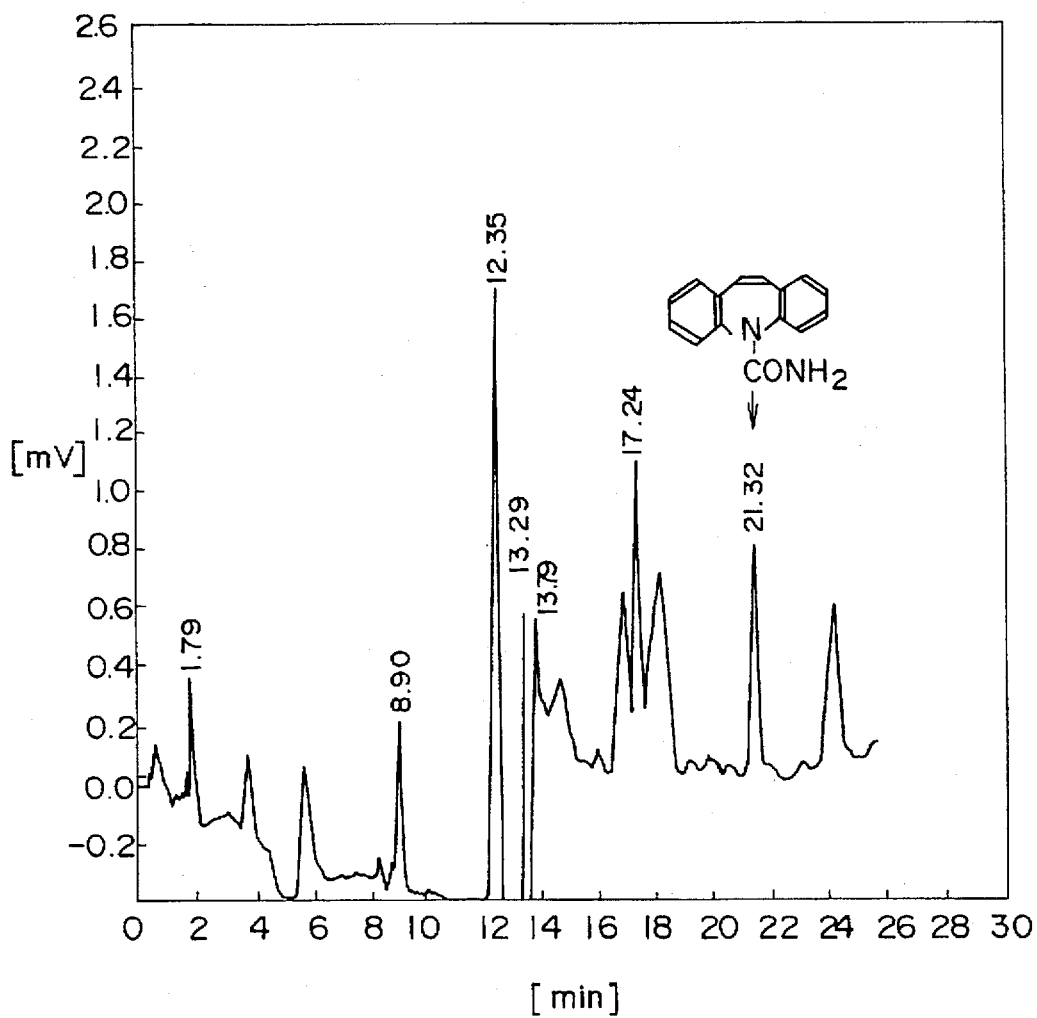
FIG. 34 is a diagram showing an example of the liquid chromatographic analysis conducted by the liquid chromatograph of the seventh embodiment of the present invention.

FIG. 34 shows the result of analysis of carbamabipine used for an antipileptic.

The analysis was made based upon the construction of the columns of:

Column 40 column:
        inner diameter=4.0 mm
        length=10 mm
        capsule pack=MF cartridge column
    mobile phase:
        0.1M buffered phosphorous acid;

Column 40a column:
        inner diameter=2.0 mm
        length=35 mm
        Capcell Pak (trade name)=phenyl
    mobile phase:
        0.1M phosphate buffer and acetonitrile, with ratio of 85:15;

Column 16 column:
        inner diameter=1.5 mm
    length:
        250 mm
        Capcell Pak=phenyl
    mobile phase:
        0.1M phosphate buffer and acetonitrile, with ratio of 85:15;

wherein the analysis was carried out according to the steps of:

(1) holding the valve 10A of FIG. 32 at the A-position shown in FIG. 33A for 1.8 minutes from the start of the analysis, while holding the flow rate of the pump 25 at 0.5 ml/min and simultaneously holding the flow rate of the pump 26 at 0.1 ml/min;

(2) holding the valve 10A of FIG. 32 at the B-position shown in FIG. 33B after the step (1), until 12 minutes has passed from the start of the analysis, with the flow rate of the pump 25 at 0.25 ml/min and simultaneously holding the flow rate of the pump 26 at 0.1 ml/min; and (3) holding the valve 10A of FIG. 32 at the A-position of FIG. 33A again after the step (2), while holding the flow rate of the pump 25 at 0.5 and simultaneously holding the flow rate of the pump 26 at 0.1 ml/min.

In the analysis, the detection is made by the detector 17 that detects an ultraviolet absorption having a wavelength of 254 nm. The separation was made at 40° C. for the amount of injected sample of 100 μl.

FIG. 34 shows the result of the analysis obtained by the detector 17. As will be seen clearly from FIG. 34, the peak of the target compound of appears with an excellent S/N ratio in correspondence to the time of 21.32 minutes from the start of the detection.

The present invention is by no means limited to the construction that uses only three columns, but is applicable also in the case where four or more columns are used.

Further, the present invention is not limited to the embodiments described heretofore, but various variations and modifications may be made without departing from the scope of the invention.

What is claimed is:

1. A liquid chromatograph, comprising:

a pump for pumping a solvent;

a separation column supplied with a sample solution for separating a sample contained therein, said separation column being filled with a first column packing material;

detection means for detecting said sample separated by said separation column;

sample injection means supplied with said solvent with said pump for injecting a sample to said solvent to produce a sample solution, said sample solution containing said sample in said solution;

a pre-column provided between said injection means and said separation column, said pre-column being supplied with said sample solution from said sample injection means for concentrating said sample to produce a concentrated sample solution, said pre-column supplying said concentrated sample solution to said separation column as said sample solution;

said pre-column having a volumetric capacity less than 2 milliliters;

wherein said pre-column is filled with a second column packing material, said second column packing material being different from said first column packing material and comprising a porous medium covered by a silicone polymer having a Si—R bond and a Si—R' bond, wherein R represents a hydrophobic group and R' represents a hydrophilic group.

2. A liquid chromatograph as claimed in claim 1, wherein said hydrophilic group R' includes a hydroxyl group.

3. A liquid chromatograph as claimed in claim 1, wherein said hydrophobic group R includes a hydrocarbon group containing 1–18 carbon atoms.

* * * * *

UNITED STATES PATENT AND TRADEMARK OFFICE
CERTIFICATE OF CORRECTION

PATENT NO. : 5,738,783
DATED : April 14, 1998
INVENTOR(S) : Osamu Shirota, et. al.

It is certified that error appears in the above-identified patent and that said Letters Patent is hereby corrected as shown below:

| Column | Line | |
|---|---|---|
| 6 | 7 | Change "phenyl-alanine" to --phenylalanine--. |
| 12 | 63 | Change "FIG. 21 ," to --FIG. 21,--. |
| 13 | 1 | Change "iS" to --is--. |
| 14 | 56 | Change "$24_{1\text{-}246}$" to --$24_1$-$24_6$--. |
| 14 | 67 | Change "$24_2$." to --$24R_2$.--. |
| 21 | 21 | At end of line, insert --(4)--. |
| 23 | 60 | Change "1-4car-" to --1-4 car- --. |
| 24 | 45 | After "oxide" delete "to oxide--. |
| 26 | 20 | Change "-hydrophitic" to -- -hydrophilic --. |
| 29 | 53 | After "column" insert --16,--. |
| 30 | 50 | After "0.5" insert --ml/min--. |

Signed and Sealed this

Twentieth Day of October, 1998

Attest:

BRUCE LEHMAN

*Attesting Officer*     *Commissioner of Patents and Trademarks*